(12) United States Patent
Katayama et al.

(10) Patent No.: US 11,419,871 B2
(45) Date of Patent: Aug. 23, 2022

(54) THERAPEUTIC AGENT FOR LUNG CANCER THAT HAS ACQUIRED EGFR-TKI RESISTANCE

(71) Applicant: JAPANESE FOUNDATION FOR CANCER RESEARCH, Tokyo (JP)

(72) Inventors: Ryohei Katayama, Tokyo (JP); Ken Uchibori, Tokyo (JP); Naoya Fujita, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 0 days.

(21) Appl. No.: 17/014,011

(22) Filed: Sep. 8, 2020

(65) Prior Publication Data
US 2020/0397786 A1    Dec. 24, 2020

Related U.S. Application Data

(62) Division of application No. 16/302,207, filed as application No. PCT/JP2017/018573 on May 17, 2017, now Pat. No. 10,813,933.

(30) Foreign Application Priority Data

May 17, 2016 (JP) ................................ 2016-098947
Dec. 9, 2016 (JP) ................................ 2016-239889

(51) Int. Cl.
| | |
|---|---|
| *A61K 31/506* | (2006.01) |
| *A61K 31/662* | (2006.01) |
| *G01N 33/574* | (2006.01) |
| *C12Q 1/68* | (2018.01) |
| *A61P 35/00* | (2006.01) |
| *A61K 45/06* | (2006.01) |

(52) U.S. Cl.
CPC .......... *A61K 31/506* (2013.01); *A61K 31/662* (2013.01); *A61P 35/00* (2018.01); *C12Q 1/68* (2013.01); *G01N 33/574* (2013.01); *A61K 45/06* (2013.01)

(58) Field of Classification Search
CPC .... A61K 31/506; A61K 31/662; A61K 45/06; A61P 35/00
See application file for complete search history.

(56) References Cited

U.S. PATENT DOCUMENTS

| | | | | |
|---|---|---|---|---|
| 7,678,373 B2 * | 3/2010 | Desnoyers | ............. | C07K 16/22 |
| | | | | 424/145.1 |
| 10,385,019 B2 * | 8/2019 | Gray | .................... | C07D 209/46 |
| 10,813,933 B2 * | 10/2020 | Katayama | ............... | A61P 35/00 |
| 2014/0024620 A1 | 1/2014 | Dalgarno et al. | | |

FOREIGN PATENT DOCUMENTS

| | | |
|---|---|---|
| JP | 2013-539795 | 10/2013 |
| JP | 2014-177456 | 9/2014 |
| WO | 2009/143389 | 11/2009 |
| WO | 2014/140989 | 9/2014 |
| WO | 2015/097621 | 7/2015 |

OTHER PUBLICATIONS

"Future Design of Cancer Incidence in Japan", Prediction by 2020 based on Bayesian Poisson Cohort Model Analysis, with English translation, 19 pages.
Schiller, et al. , "Comparison of Four Chemotherapy Regimens for Advanced Non-Small-Cell Lung Cancer", The Mew England Journal of Medicine, 2002, vol. 346, No. 2, p. 92-98, 7 pages.
Ohe, et al., "Randomized Phase III Study of Cisplatin Plus Irinotecan Versus Carboplatin Plus Paclitaxel, Cisplatin Plus Gemcitabine, and Cisplatin Plus Vinorelbine for Advanced Non-Small-Cell Lung Cancer: Four Arm Cooperative Study in Japan", Annals of Oncology, 2007, vol. 8, p. 317-323, 7 pages.
Paz-Ares, "Paramount: Final Overall Survival Results of the Phase III Study of Maintenance Pemetrexed Versus Placebo Immediately After Induction Treatment with Pemetrexed Plus Cisplatin for Advanced Nonsquamous Non-Small-Cell Lung Cancer", Journal of Clinical Oncology, 2013, vol. 31, No. 23, p. 2895-2902, 10 pages.
Sandler, et al., "Paclitaxel-Carboplatin Alone or with Bevacizumab for Non-Small-Cell Lung Cancer", The New England Journal of Medicine, 2006, vol. 355, p. 2542-2550, 10 pages.
Paez, et al., "EGFR Mutations in Lung Cancer: Correlation with Clinical Response to Gefitinib Therapy", Science, 2004, vol. 304, p. 1497-1500, 5 pages.
Lynch, et al., Activating Mutations in the Epidermal Growth Factor Receptor Underlying Responsiveness of NonSmall-Cell Lung Cancer to Gefitinib, The New England Journal of Medicine, 2004, vol. 350, No. 21, p. 2129-2139, 11 pages.
Mitsudomi, et al., "Epidermal Growth Factor Receptor in Relation to Tumor Development: EGFR Gene and Dancer", The FEBS Journal, 2010, 277, p. 301-308, 8 pages.
Mok, et al., "Gefitinib or Carboplatin-Paclitaxel in Pulmonary Adenocarcinoma", The New England Journal of Medicine, 2009, vol. 361, No. 10, p. 947-957, 11 pages.
Maemondo, et al., "Gefitinib or Chemotherapy for Non-Small-Cell Lung Cancer with Mutated EGFR", The New England Journal of Medicine, 2010, vol. 362, p. 2380-2388, 9 pages.
Mitsudomi, et al., "Gefitinib Versus Cisplatin Plus Docetaxel in Patients with Non-Small-Cell Lung Cancer Harbouring Mutations of the Epidermal Growth Factor Receptor (WJTOG3405): an Open Label, Randomised Phase 3 Trial", Lancet Oncol. 2010, vol. 11, p. 121-128, 8 pages.

(Continued)

*Primary Examiner* — Deepak R Rao
(74) *Attorney, Agent, or Firm* — Rankin, Hill & Clark LLP

(57) ABSTRACT

A drug containing, as an active ingredient, a compound represented by ALK inhibitors such as brigatinib, AP26113-analog, and AZD3463 has been found to be effective against a non-small cell lung cancer having a point mutation at C797S in EGFR which has acquired a resistance to chemotherapy agents. Further, the drug used in combination with an anti-EGFR antibody demonstrates a notable suppression effect on the tumor growth. The drug has a potential to be a therapeutic agent effective against a non-small cell lung cancer which is resistant to gefitinib, a first generation therapeutic agent and osimertinib, a third generation therapeutic agent.

10 Claims, 16 Drawing Sheets
Specification includes a Sequence Listing.

(56) References Cited

OTHER PUBLICATIONS

Kris, et al., "Using Multiplexed Assays of Oncogenic Drivers in Lung Cancers to Select Targeted Drugs", NIH, Jama, 2014, vol. 311, p. 1998-2006, 18 pages.

Yu, et al., "Analysis of Tumor Specimens at the Time of Acquired Resistance to EGFR TKI Therapy in 155 Patients with EGFR Mutant Lung Cancers", NIH, Clin. Cancer Res , 2013, vol. 19, p. 2240-2247, 18 pages.

Janjigian, et al., "Dual Inhibition of EGFR with Afatinib and Cetuximab in Kinase Inhibitor-Resistant EGFR-Mutant Lung Cancer with and without T790M Mutations", Cancer Discovery, 2014, vol. 4, p. 1036-1045, 11 pages.

Cross, et al., "AZD9291, an Irreversible EGFR TKI, Overcomes T790M-Mediated Resistance to EGFR Inhibitors in Lung Cancer", Cancer Discov., 2014, vol. 4, p. 1046-1061, 17 pages.

Janne, et al., "AZD9291 in EGFR Inhibitor-Resistant Non-Small-Cell Lung Cancer", The New England Journal of Medicine, 2015, vol. 372. p. 1689-1699, 11 pages.

Thress, et al., "Acquired EGFR C797S Mediates Resistance to AZD9291 in Advanced Non-Small Cell Lung Dancer Harboring EGFR T790M", Nat Med., 2015, vol. 21(6), p. 560-562, 11 pages.

Eberlein, et al., "Acquired Resistance to the Mutant-Selective EGFR Inhibitor AZD9291 is Associated with ncreased Dependence on RAS Signaling in Preclinical Models", Cancer Research. 2015, vol. 75, p. 2489-2500, 13 pages.

Ercan, et al., "EGFR Mutations and Resistance to Irreversible Pyrimidine-Based EGFR Inhibitors", Clinical Cancer Research, 2015, vol. 21, p. 3913-3923, 12 pages.

Niederst, et al., "The Allelic Context of the C797S Mutation Acquired upon Treatment with Third-Generation EGFR Inhibitors Impacts Sensitivity to Subsequent Treatment Strategies", Clinical Cancer Research, 2015, vol. 21, p. 3924-3933, 11 pages.

Jia, et al., "Overcoming EGFR T790M and C797S Resistance with Mutant-Selective Allosteric Inhibitors", Nature, 2016, vol. 534, p. 129-132, 28 pages.

Li, et al., "Structural Basis for Inhibition of the Epidermal Growth Factor Receptor by Cetuximab", Cancer Cell, 2005, vol. 7, p. 301-311, 11 pages.

Sickmier, et al. "The Panitumumab EGFR Complex Reveals a Binding Mechanism that Overcomes Cetuximab Induced Resistance", PLOS ONE, 2016, DOI: 10.1371/journal.pone.0163366, 11 pages.

Brower, et al., "Centerfor Drug Evaluation and Research", 2015, FDA Pharmacology Review(s), Reference ID 3796870, 70 pages.

Miret, et al., "AP26113, a Potent ALK Inhibitor, is also active against EGFR T790M in Mouse Models of NSCLC", Journal of Thoracic Oncology, 2011, vol. 6, No. 6, Suppl.2, p. S577-S578, Abstract No. MO11.12, Methods, Results, 2 pages.

Rivera, et al., "Abstract 1794: AP26113 is dual ALK/EGFR Inhibitor: Characterization against EGFR T790M in Cell and Mouse Models of NSCLC", Cancer Research, 2012, vol. 72, No. Suppl. 8, Methods, Results, 2 pages.

Camidge, et al., First-in-human dose-finding study of the ALK/EGFR inhibitor AP26113 in patients with advanced malignancies: Updated Results, J. Clin. Oncol. 2013, vol. 31, No. 15, Suppl, Abstract No. 8031, Background Results, 3 pages.

Drew, et al., "Abstract 4465: Concurrent Roles for IGF1R and EGFR in Driving Acquired Resistance to Crizotinib and Ability to Overcome with a Combination of the ALK/IGR1R Inhibitor AZD3463 and Iressa", Cancer Research, 2013, vol. 73, Issue 8, 2 pages.

Thress, et al. "Acquired EGFR C797S Mediates Resistance to AZD9291 in Advanced Non-Small Cell Lung Cancer Harboring EGFR T790M", Nat. Med., 2015, vol. 21, No. 6, p. 560-562, 11 pages.

English Translation of Written Opinion dated Jun. 27, 2017, 7 pages.

Gettinger, et al., "Activity and safety of brigatinib in ALK-rearranged non-small-cell lung cancer and other malignancies: a single-arm, open label, phase 1/2 trial", Lancet Ongology, Dec. 2016, vol. 17, pp. 1683-1696.

Patel, et al., "Recent updates on third generation EGFR inhibitors and emergence of fourth generation EGFR nhibitors to combat C797S resistance", European Journal of Medicinal Chemistry, 142 (2017), pp. 32-47.

Crescenzo et al., "Anaplastic lymphoma kinase inhibitors", Current Opinion in Pharmacology, 2015, vol. 23, pp. 39-44.

"A Study to Evaluate the Efficacy of Brigatinib (AP26113) in Participants With Anaplastic Lymphoma Kinase (ALK)-Positive, Non-small Cell Lung Cancer (NSCLC) Previously Treated With Crizotinib", U.S. National Library of Medicine, Mar. 24, 2014, pp. 1-13.

Zhang et al., "Abstract 781: The potent ALK inhibitor AP26113 can overcome mechanisms of resistance to first-and second-generation ALK TKIs in preclinical models", Aug. 2015, DOI: 10.1158/1538-7445 AM2015-781, 5 pages.

Yu, et al., "Mutation-Specific Antibodies for the Detection of EGFR Mutations in Non-Small-Cell Lung Cancer", Clinical Cancer Research May 1, 2009, vol. 15, pp. 3023-3028.

Asano et al., "Detection of EGFR Gene Mutation in Lung Cancer by Mutant-Enriched Polymerase Chain Reaction Assay", Clinical Cancer Research, Jan. 1, 2006, vol. 12, pp. 43-48.

Uchibori, et al., "Brigatinib combined with anti-EGFR antibody overcomes osimertinib resistance in EGFR-mutated non-small-cell lung cancer", Nature Communications, Mar. 13, 2017, pp. 1-16.

Yu et al., "Acquired Resistance of EGFR-Mutant Lung Cancer to a T79OM-Specific EGFR Inhibitor: Emergence of a Third Mutation (C797S) in the EGFR Tyrosine Kinase Domain", JAMA Oncology, Oct. 2015, vol. 1, No. 7, pp. 982-984.

Yu et al., "Second-Generation Epidermal Growth Factor Receptor Tyrosine Kinase Inhibitors in Lung Cancers", Journal of the National Comprehensive Cancer Network, Feb. 2013, vol. 11, No. 2 pp. 161-169.

\* cited by examiner

Fig.15A
Fig.15B
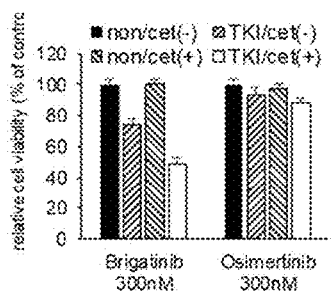
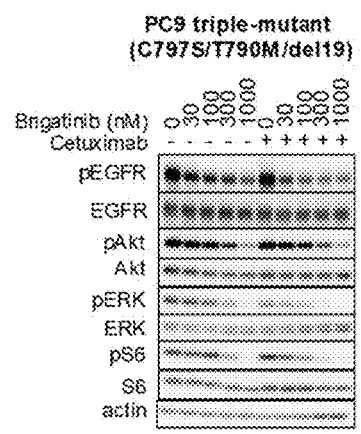
Fig.15C
Fig.15D
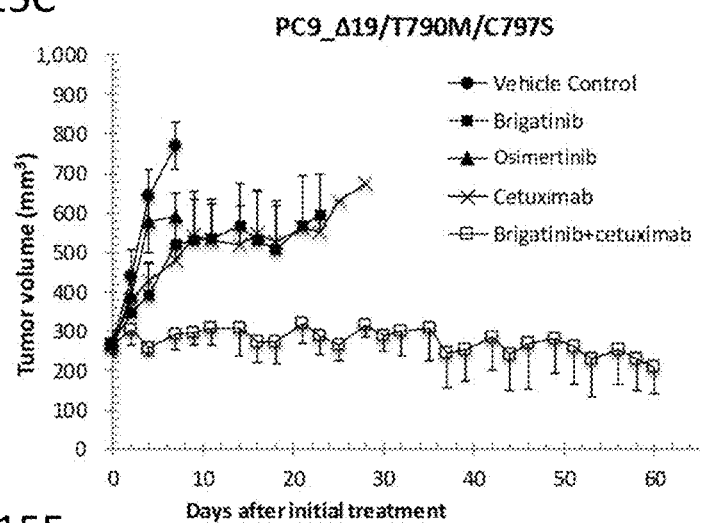
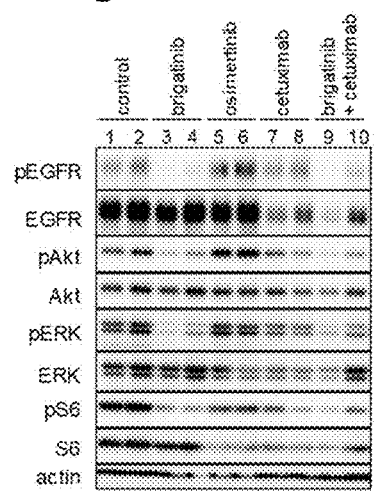
Fig.15E
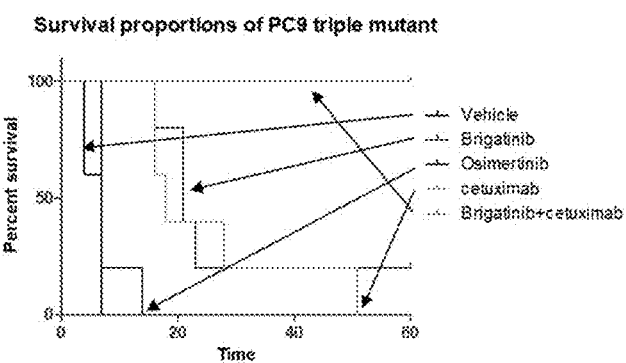

Fig.18B Survival proportions of PC9 triple mutant

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: PCR primer

<400> SEQUENCE: 1
ccgtgcagct catcatccag ctcatgccct tc                                    32

<210> SEQ ID NO 2
<211> LENGTH: 32
<212> TYPE: DNA
<213> ORGANISM: Artificial Sequence
<220> FEATURE:
<223> OTHER INFORMATION: PCR primer

<400> SEQUENCE: 2
gaagggcatg agctgcatga tgagctgcac gg                                    32

<210> SEQ ID NO 3
<211> LENGTH: 28
<212> TYPE: DNA
<213> ORGANISM: Artificial Sequence
<220> FEATURE:
<223> OTHER INFORMATION: PCR primer

<400> SEQUENCE: 3
catgcccttc ggctccctcc tggagcta                                         28

<210> SEQ ID NO 4
<211> LENGTH: 27
<212> TYPE: DNA
<213> ORGANISM: Artificial Sequence
<220> FEATURE:
<223> OTHER INFORMATION: PCR primer

<400> SEQUENCE: 4
tagtccagga gggagccgaa gggcatg                                          27
```

THERAPEUTIC AGENT FOR LUNG CANCER THAT HAS ACQUIRED EGFR-TKI RESISTANCE

TECHNICAL FIELD

The present invention relates to, in a therapy for a lung cancer which has an EGFR (Epidermal Growth Factor Receptor) gene mutation, a therapy for a cancer which has acquired the resistance to EGFR-TKI (EGFR tyrosine kinase inhibitor). Particularly, the present invention relates to a therapeutic agent that is effective against a cancer having acquired the resistance to gefitinib, erlotinib, or afatinib which is selected as the first therapeutic agent for an EGFR gene mutation-positive non-small cell lung cancer and subsequently also has acquired the resistance to osimertinib.

BACKGROUND ART

The mortality from lung cancers in Japan was 7.9 for male and 3.2 for female per population of 100,000 in 1960 but has been steadily increasing in recent years. According to the announcement by National Cancer Center Japan, the estimated number of deaths from lung cancers for 2015 is 77,200 which ranked first in the site-specific cancer deaths. The number of the deaths for males is 55,300 which ranked first and for women is 21,900 which ranked second.

According to the report by Ohno and Nakamura et al. in 2004, the estimated number of new patients with lung cancers for 1 year of 2020 in Japan was about 91,000 for male and about 34,000 for female, however according to the announcement by National Cancer Center Japan described above, the number of new patients of 97,000 for male and 42,800 for female were already estimated at the time of 2015 (Non Patent Literature 1), concerning that the numbers may exceed the estimation at the time of 2020, whereby the development of therapeutic methods has been an serious issue. The number of deaths from lung cancers are increasing worldwide. According to the statistics by Union for International Cancer Control (UICC), the number of deaths from lung cancers is the highest among the cancers and said to be equivalent to ⅕ of all the deaths from cancers.

Lung cancers are roughly classified into non-small cell lung cancers and small cell lung cancers, and the non-small cell lung cancers account for about 80 to 85% in the total lung cancers and the small cell lung cancers account for about 10 to 15%. In the unresectable advanced non-small cell lung cancers, chemoradiotherapy is standard in the case where full dose irradiation is tolerable, whereas the standard therapy for the non-small cell lung cancers at the full dose irradiation intolerable stage IIIB and stage IV is chemotherapy. In 1995, it was revealed that chemotherapy groups, wherein cisplatin (CDDP) and an existing anticancer agent were used in combination, improved the median survival time (MST) for 6 to 8 weeks and the 1 year survival rate for 15% when compared to best supportive care (BSC) groups. Based on the results of the subsequently conducted 4-group comparative Phase III (ECOG1594) trial by Eastern Cooperative Oncology Group (ECOG) (Non Patent Literature 2) and FACS (Four Arms Cooperative Study) test (Non Patent Literature 3) in Japan, some of the combinations of platinum-based preparations and a third generation anticancer agent were established as the standard therapy for non-small cell lung cancers. Further, agents effective against non-squamous cell cancers such as Pemetrexed (BMDJ, PARAMOUNT test (Non Patent Literature 4)) and Bevacizumab (ECOG4599 test (Non Patent Literature 5)) were developed and thus the extension of survival time was achieved, whereby these agents have held the prominent position in the therapy for lung adenocarcinoma. However, the survival time extension effect somehow managed to increase about half a year to a little less than 1 year on top of about 1 year of the survival time extension effect by the cytotoxic anticancer agents demonstrated in the above ECOG test and FACS test due to the appearance of Pemetrexed and Bevacizumab, but further advancement was not made and at a standstill.

On the other hand, the efficacy of EGFR-TKI has been demonstrated. In 2004, the presence of an EGFR gene mutation in the non-small cell lung cancer was reported, thereby suggesting that the existence of an EGFR gene mutation and the effect of EGFR-TKI are associated (Non Patent Literatures 6 and 7). EGFR-TKI is an agent that binds to the ATP binding site of EGFR tyrosine kinase and inhibits the autophosphorylation of EGFR to thereby inhibit the signal transductions of EGFR. Gefitinib (product name: Iressa (registered trademark)), erlotinib (product name: Tarceva (registered trademark)), and afatinib (product name: Giotrif (registered trademark)) are approved in Japan.

Most of the EGFR gene mutations occur in exons 18 to 21, which is the tyrosine kinase region, and it is revealed that the exon 19 deletion mutation accounts for 48%, L858R (substitution of leucine at the 858th with arginine. Hereinafter, point mutations are described by the position of an amino acid and the sequences before and after a substitution) accounts for 43%, and others such as G719X and rare mutations account for about 15%.

The exon 19 deletion mutation is most commonly the simple deletion mutation at the site around ELREA 5 amino acids of 746 to 750 but includes an extremely large variety of mutations such as those involving the number of deleted amino acids and those involving an amino acid substitution (Non Patent Literature 8).

Gefitinib, i.e., EGFR-TKI, the development of which advanced first, demonstrated a tumor regression effect after the secondary therapy via some clinical tests. However, gefitinib was known to have cases where impressive effects were often recognized but the true predictive factor of effectiveness was not clear at first. Additionally, a significant life-extension effect was not demonstrated in the phase III trial on study cases for which patients were not selected.

However, when patient selection was carried out for a case with the clinical background (non-smokers, Asian, adenocarcinoma) to which the efficacy of EGFR-TKI is expected and the phase III trial, i.e., IPASS (Iressa Pan Asia Study) wherein gefitinib and a combination chemotherapy of carboplatin (CBDCA)/paclitaxel (PTX) are compared was carried out, the PFS (progression-free survival) in the gefitinib group was demonstrated to have been significantly extended (Non Patent Literature 9). In the IPASS study, the existence of EGFR gene mutations is partially analyzed, and PFS was significantly longer (HR (hazard ratio)=0.48, gefitinib group 9.5 months, CBDCA+PTX group 6.3 months) in the EGFR gene mutation-positive group but PFS with gefitinib was shorter (HR=2.85, the gefitinib group 1.5 months, CBDCA+PTX group 5.5 months) in the mutation negative group despite the selection was made by the clinical background, thereby demonstrating that the EGFR gene mutation is the predictive factor of effectiveness. Thereafter, a plurality of the comparative phase III trials on the EGFR-TKI and platinum combination therapy in the primary therapy were carried out by selecting patients with the EGFR gene mutation-positive case, whereby significant PFS extension by EGFR-TKI was demonstrated in all the studies which have been reported so far.

Of these, NEJ002 trial, which is the comparative phase III trial on gefitinib and CBDCA+PTX carried out in Japan (Non Patent Literature 10) and WJTOG3405 trial, which is the comparative phase III trial on gefitinib and the combination therapy of CDDP+docetaxel (DTX) (Non Patent Literature 11) demonstrated that PFS is significantly extended in the gefitinib groups (NEJ002; HR=0.30, gefitinib group 10.8 months, CBDCA+PTX group 5.4 months, WJTOG3405; HR=0.520, gefitinib group 9.6 months, CDDP+DTX group 6.6 months). In these trials, the median overall survival demonstrated were 34.8 months in WJTOG3405 and 27.7 months in NEJ002 in the subsequent reports, whereby the importance of administering EGFR-TKI to EGFR gene mutation-positive patients is widely demonstrated.

Starting with the discovery of such an EGFR-TKI, proto-oncogenes to be therapeutic targets such as EML4-ALK translocation fusion, RET translocation fusion, ROS1 translocation fusion, HER2 mutation, and BRAF mutation were discovered one after another in lung adenocarcinoma, and the development of corresponding therapeutic agents provides great advantages for patients with respective diseases. The benefits of precise detection of existence of a proto-oncogene and providing a therapy with a suitable corresponding molecular target drug were reported by Kris et al. in 2014, which are now the essential for the lung cancer therapy (Non Patent Literature 12).

As described above, the impacts on the clinical practice provided by the molecule target drugs are hardly replaceable. Although the remarkable therapeutic effect has seen at the early stage from the beginning it lasts only about one to several years at longest, and disease relapse in substantially all the cases by the appearance of the acquired resistance. Studies on the mechanism of acquired resistance after the administration of gefitinib and erlotinib, which are the first generation drugs for the EGFR gene mutation-positive lung cancers, have been performed. According to Non Patent Literature 13, it is revealed that about 60% is the mutation called the gatekeeper mutation which occurs at a binding site of an inhibitor, wherein threonine at position 790 present in the ATP binding site of the EGFR protein is replaced with methionine to thereby reduce the ATP binding inhibitory potency of the inhibitor. At first, a plurality of the therapy developments for the gefitinib and erlotinib resistance cases were carried out in various clinical trials but none of them was able to demonstrate sufficiently beneficial therapeutic effects, and even the combination therapy of afatinib and cetuximab which was the only therapy provided a response rate of 29% had severe adverse events and has not been applied at clinical sites (Non Patent Literature 14).

Subsequently, the development of covalently bound EGFR-TKI targeting T790M positive EGFR was started one after another. The most precedently developed osimertinib (AZD9291, product name: Tagrisso (registered trademark)) had the results of the 1/2 phase trial reported at the 2014 ASCO annual meeting (Non Patent Literatures 15 and 16), followed by announcements of favorable therapeutic outcomes in the T790M positive EGFR gene mutation-positive lung cancer one after another and was approved by U.S. FDA in November 2015 and approved in Japan during the year 2016 with an insurance coverage.

CITATION LIST

Non Patent Literature

Non Patent Literature 1: Ohno Yuko, Nakamura Takashi et al. Prediction of cancer incidence in Japan—Projections up to 2020 based on the analyses using a Bayesian Poisson cohort model: Cancer Statistics—incidence/death/prognosis—2004, Oshima A et al., (eds), 2004 Shinohara Shuppan.
Non Patent Literature 2: Shiller, J. H., et al., N. Engl. J. Med., 2002, Vol. 346, p. 92-98.
Non Patent Literature 3: Ohe Y., et al., Ann. Oncol., 2007, Vol. 8, p. 317-323.
Non Patent Literature 4: Paz-Ares L. G., et al., J. Clin. Oncol., 2013, Vol. 31, p. 2895-2902.
Non Patent Literature 5: Sandler, A., et al., N. Engl. J. Med., 2006, Vol. 355, p. 2542-2550.
Non Patent Literature 6: Paez, J. G., et al., Science, 2004, Vol. 304, p. 1497-1500.
Non Patent Literature 7: Lynch, T. J., et al., N. Engl. J. Med., 2004, 350, p. 2129-2139.
Non Patent Literature 8: Mitsudomi T., et al., The FEBS J., 2010, 277, p. 301-308.
Non Patent Literature 9: Mok, T. S., et al., N. Engl. J. Med., 2009, Vol. 361, p. 947-957.
Non Patent Literature 10: Maemondo, M., et al., N. Engl. J. Med., 2010, Vol. 362, p. 2380-2388.
Non Patent Literature 11: Mitsudomi, T., et al., Lancet Oncol. 2010, Vol. 11, p. 121-128.
Non Patent Literature 12: Kris M. G., et al., JAMA, 2014, Vol. 311, p. 1998-2006.
Non Patent Literature 13: Yu, H. A., et al., Clin. Cancer Res., 2013, Vol. 19, p. 2240-2247.
Non Patent Literature 14: Janjigian, Y. Y., et al., Cancer Discov., 2014, Vol. 4, p. 1036-45.
Non Patent Literature 15: Cross, D. A., et al., Cancer Discov., 2014, Vol. 4, p. 1046-1061.
Non Patent Literature 16: Janne, P. A., et al., N. Engl. J. Med., 2015, Vol. 372, p. 1689-1699.
Non Patent Literature 17: Thress, K. S., et al. Nat. Med., 2015, Vol. 21(6), pp. 560-562.
Non Patent Literature 18: Eberlein, C. A., et al., Cancer Res., 2015, Vol. 75, p. 2489-2500.
Non Patent Literature 19: Ercan D., et al., Clin. Cancer Res., 2015, Vol. 21, p. 3913-23.
Non Patent Literature 20: Niederst, M. J., et al., Clin. Cancer Res., 2015, Vol. 21, p. 3924-3933.
Non Patent Literature 21: Jia, Y., et al., Nature, 2016, Vol. 534, p. 129-132.
Non Patent Literature 22: Li, S., et al., Cancer Cell, 2005, Vol. 7, p. 301-311.
Non Patent Literature 23: Sickmier, E. A., et al., PLOS ONE, 2016,DOI:10.1371/journal.pone.0163366.
Non Patent Literature 24: Brower, M. E., et al., 2015, FDA Pharmacology Review(s), Reference ID: 3796870.

SUMMARY OF INVENTION

Technical Problem

It is considered that, due to the appearance of osimertinib to the clinic, the importance of TKI as the therapy plan for the EGFR gene mutation-positive lung cancers definitely increases. However, the resistance mechanism thereof together with good therapeutic effects were already reported in 2015. In the clinical trial cases of osimertinib targeting the T790M positive EGFR lung cancers, the C797S mutation was detected from cell-free tumor DNA in the plasma of a patient who has become resistant to the osimertinib (Non Patent Literature 17). From other patients, the occurrence of 3 different kinds of resistances by the disappearance of the T790M mutation were reported as other patterns (Non Patent Literatures 18 and 19), which are also apparently verified by reports based on the findings obtained by the clinical trials on CO-1686, which is another third generation EGFR-TKI.

For the resistance mechanisms of the T790M disappearance and the bypass pathway dependency, combination therapies can be assumed as an overcoming method based on the nature thereof, however for the appearance of the C797S mutation, effective measures are not clearly suggested at present. According to the study on the appearance of C797S on the identical gene to T790M (cis) or the allele (trans) by Niederst et al., it is suggested that the combination of the first generation EGFR-TKI (gefitinib or erlotinib) and the third generation EGFR-TKI (osimertinib, etc.) is effective in the case of trans, whereas the existing TKI is totally ineffective in the case of cis (Non Patent Literature 20). Therefore, it is anticipated that overcoming of cis is particularly difficult. Additionally, it is not clear at present whether or not the appearance of T790M and C797S can be reproduced on trans clinically.

The acquired resistance due to the C797S mutation appearance, while only the insufficient total number of the third generation resistance cases itself being accumulated needs to be considered, is presumed to be equivalent to 4 to 5% of the total lung cancer when referred to the frequency of the reports made at the 2015 WCLC (World Conference on Lung Cancer). Such a frequency is approximately the same as ALK positive lung cancer cases and considered to account for a certain extent of clinical proportion. Thus, it is a clinically important issue to establish a therapeutic method for this group.

Recently, it is revealed that EAI045 is effective as an allosteric inhibitor on the EGFR mutant having mutations of L858R, T790M, and C797S. EAI045 has been confirmed to demonstrate a notable inhibitory effect on the tumor growth in mouse models when administered in combination with cetuximab, which is an anti-EGFR antibody drug (Non Patent Literature 21). However, EAI045 is a compound in the development stage and cannot be used immediately in actual clinical practice. Additionally, EAI045 is not effective on the exon 19 deletion mutation which accounts for about half the number of the EGFR mutation-positive lung cancers. Thus, the present circumstance, where a therapeutic agent effective on the EGFR mutant having the C797S mutation is needed, remains unchanged.

Solution to Problem

The present invention relates to a therapeutic agent, a method for testing efficacy of a therapeutic agent and a kit.
(1) A therapeutic agent for an EGFR gene mutations-positive non-small cell lung cancer, comprising, as an active ingredient, a compound represented by general formula (I) or a pharmacologically acceptable salt thereof:

[Formula 1]

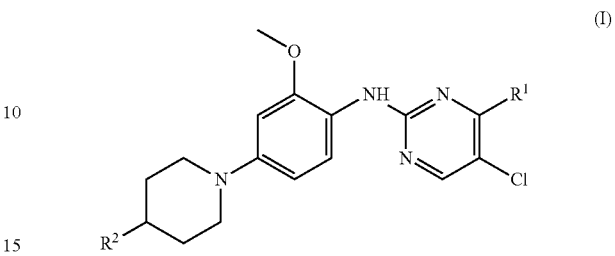

wherein $R^1$ is a group represented by the following formula (II) or (III):

[Formula 2]

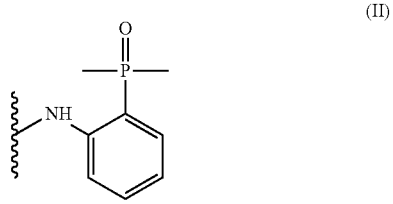

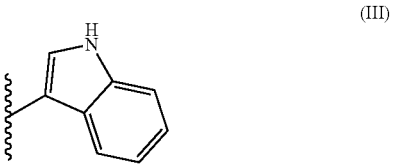

$R^2$ is —N(CH$_3$)$_2$, —NH$_2$, or a group represented by the following formula (IV):

[Formula 3]

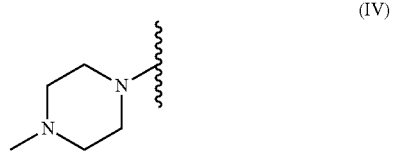

(2) The therapeutic agent for an EGFR gene mutations-positive non-small cell lung cancer according to (1), wherein the compound is brigatinib, AP26113-analog, or AZD3463.
(3) The therapeutic agent for a non-small cell lung cancer according to (1) or (2), wherein the EGFR gene mutations-positive non-small cell lung cancer is a cancer having a mutation at position 797 in EGFR.
(4) The therapeutic agent for a non-small cell lung cancer according to any one of (1) to (3), wherein the non-small cell lung cancer is a cancer having mutations at positions 797 and 790 in EGFR.
(5) The therapeutic agent for a non-small cell lung cancer according to any one of (1) to (4), which is administered in combination with an anti-EGFR antibody.
(6) A method for testing efficacy of a drug by detecting a mutation at position 797 in EGFR in an EGFR gene mutations-positive non-small cell lung cancer, the drug comprising, as an active ingredient, a compound represented by general formula (I) or a pharmacologically acceptable salt thereof:

[Formula 4]

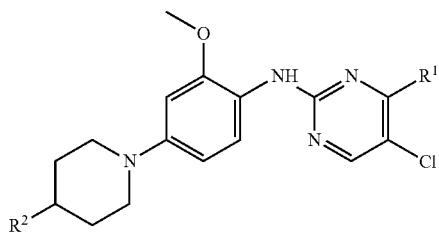

(I)

wherein $R^1$ is a group represented by the following formula (II) or (III):

[Formula 5]

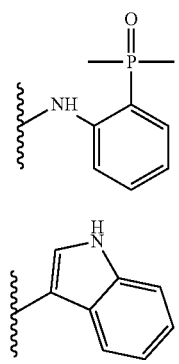

(II)

(III)

$R^2$ is —N(CH$_3$)$_2$, —NH$_2$, or a group represented by the following formula (IV):

[Formula 6]

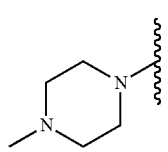

(IV)

(7) A method for testing efficacy of a drug according to (6), wherein the compound is brigatinib, AP26113-analog, or AZD3463.
(8) The method for testing efficacy of a drug according to (6) or (7), wherein the detection of a mutation at position 797 in EGFR is detection of a mutation in nucleic acid and/or protein.
(9) The method for testing efficacy of a drug according to (8), wherein the detection of a mutation in nucleic acid is carried out by PCR and the detection of a mutation in protein is carried out by an antibody.
(10) A kit for testing efficacy of a drug, comprising PCR primers or an antibody for detecting a mutation at position 797 in EGFR, the drug comprising, as an active ingredient, a compound represented by general formula (I) or a pharmacologically acceptable salt thereof:

[Formula 7]

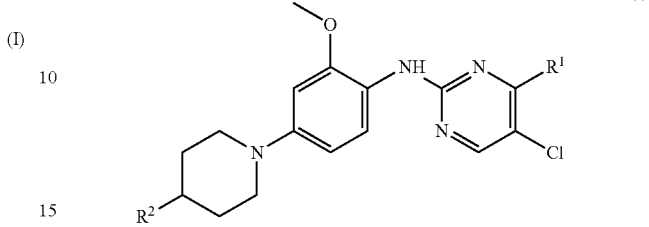

(I)

wherein $R^1$ is a group represented by the following formula (II) or (III)

[Formula 8]

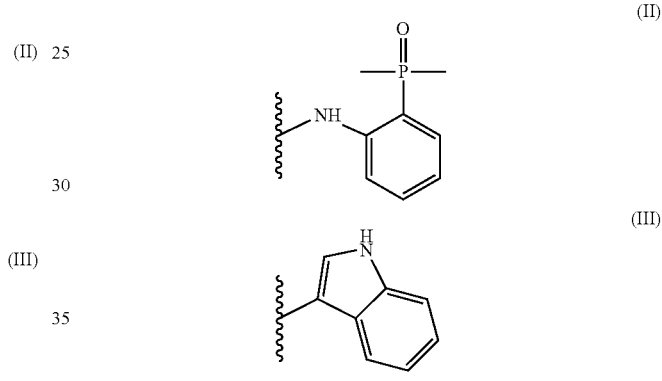

(II)

(III)

$R^2$ is —N(CH$_3$)$_2$, —NH$_2$, or a group represented by the following formula (IV)

[Formula 9]

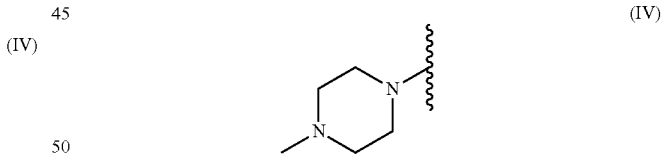

(IV)

(11) The kit for testing efficacy of a drug according to (10), wherein the compound is brigatinib, AP26113-analog, or AZD3463.
(12) The kit for testing efficacy of a drug according to (10) or (11), further comprising PCR primers or antibodies for detecting an exon 19 deletion mutation, an L858R mutation, and a T790M mutation in EGFR.
(13) A method for treatment of an EGFR gene mutations-positive non-small cell lung cancer, comprising detecting a mutation at position 797 of EGFR and administrating a therapeutic agent including a compound represented by the following general formula (I) or a pharmacologically acceptable salt thereof as an active ingredient, in combination with an anti-EGFR antibody:

[Formula 10]

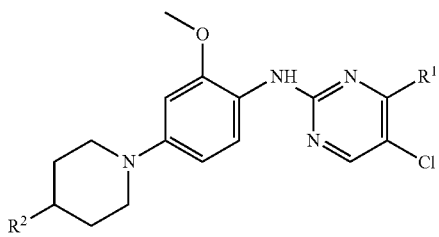

(I)

wherein R¹ is a group represented by the following formula (II) or (III):

[Formula 11]

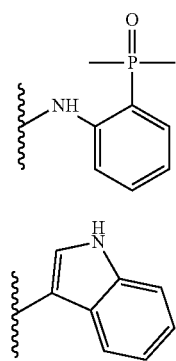

(II)

(III)

R² is —N(CH₃)₂, —NH₂, or a group represented by the following formula (IV):

[Formula 12]

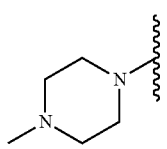

(IV)

(14) A method for treatment wherein the compound is brigatinib, AP26113-analog, or AZD3463.
(15) A method for treatment wherein the anti-EGFR antibody is cetuximab, panitumumab, or necitumumab.

The compound described in the present specification enables the therapy for a cancer which has become resistant to the third generation EGFR-TKI represented by osimertinib and has caused a mutation at position 797 in EGFR. More specifically, an EGFR gene mutation-positive non-small cell lung cancer is first treated by gefitinib, erlotinib, or afatinib. When unresponsiveness is caused by the T790M mutation in EGFR due to the therapy using these drugs, a therapy is carried out using a third generation EGFR-TKI such as osimertinib. Further, when unresponsiveness to osimertinib or the like is caused by the C797S mutation, the use of the therapeutic agent of the present invention has enabled the attainment of an excellent therapeutic effect on a non-small cell lung cancer expressing EGFR triple-mutant. The EGFR triple-mutant has acquired the C797S mutation as the third mutation, in addition to cancer causative mutation, the EGFR exon 19 deletion or the L858R mutation, and T790M, i.e., the second mutation. Furthermore, when the therapeutic agent is used in combination with an anti-EGFR antibody, stronger effects can be obtained. Particularly, the combination use with an anti-EGFR antibody is confirmed, in vivo tests, to have a cancer regression effect and expected to provide a therapeutic effect on a lung cancer which has acquired the resistance to a therapeutic agent.

BRIEF DESCRIPTION OF DRAWINGS

FIG. 15A is a drawing of the study on the combination effect of cetuximab and tyrosine kinase inhibitors on the cell viability of a triple-mutant expressing PC9 cell line.

FIG. 15B is a drawing showing the analysis on the effects of brigatinib and cetuximab on the EGFR signal transductions of the above triple-mutant cell line.

FIG. 15C is a drawing showing the effects of brigatinib, osimertinib, cetuximab, and the combination administration of brigatinib and cetuximab on mice transplanted with the above triple-mutant expressing cell line.

FIG. 15D is a drawing showing the analysis on the phosphorylation of the EGFR signal transduction pathway molecules of the above triple mutant expressing cells transplanted in mice and treated with brigatinib, osimertinib, cetuximab, and the combination of brigatinib and cetuximab.

FIG. 15E is a drawing showing the survival curves of the mice transplanted with the above triple-mutant expressing cells.

FIG. 18B is a drawing showing the survival curves of the above mice.

DESCRIPTION OF EMBODIMENTS

Figure 1:
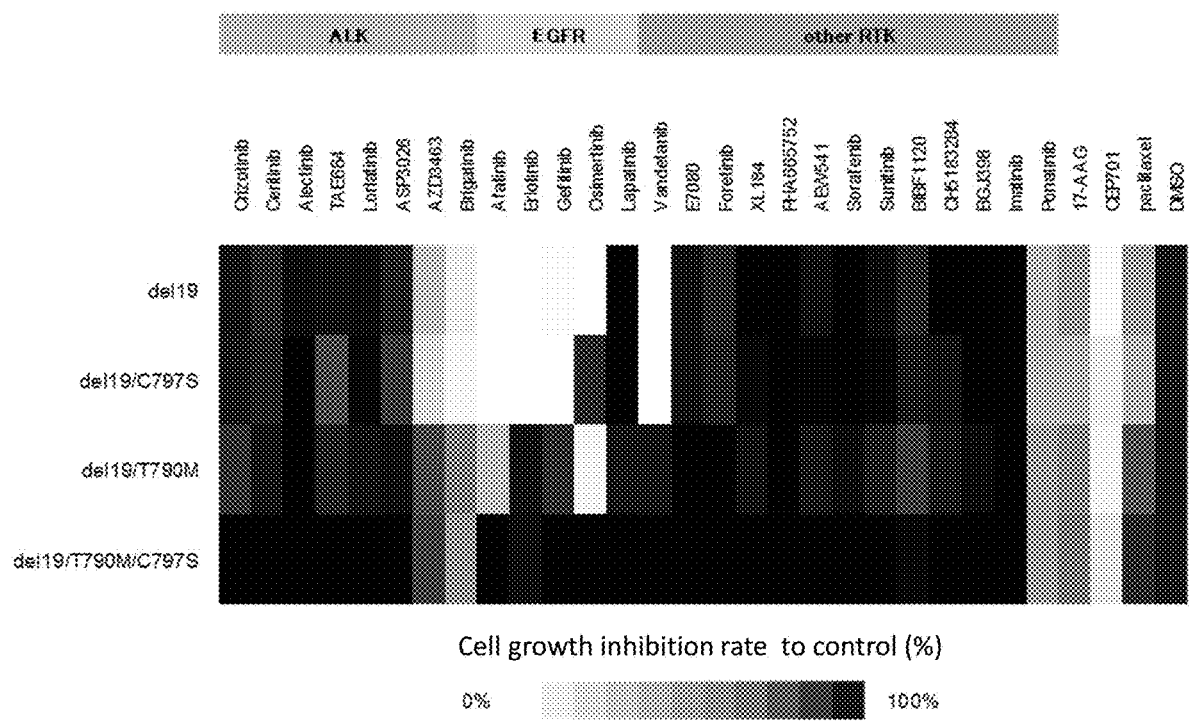
FIG. 1 is a drawing showing the screening results of agents that inhibit the growth of cell lines expressing the C797S mutant in EGFR.

Hereinafter, the compound providing an effect on a cancer which is a non-small cell lung cancer having a C797S point mutation and has acquired the resistance to a first generation EGFR-TKI represented by gefitinib and a third generation EGFR-TKI represented by osimertinib (AZD9291), a method for testing the efficacy of such a compound, and a method for treatment are described in reference to data.

The present inventors have found that an ALK inhibitor brigatinib induces the growth suppression on the cell having a point mutation of C797S which appears after the therapy with osimertinib. Focusing on that the cell which has acquired the resistance to osimertinib has the C797S mutation, the present inventors have screened a number of compounds using cell lines having both C797S and T790M mutations. As a result, the present inventors have found that ALK inhibitors represented by the following general formula suppress the cell growth.

[Formula 13]

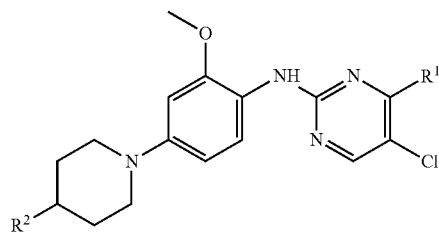

(I)

wherein $R^1$ is a group represented by the following formula (II) or (III)

[Formula 14]

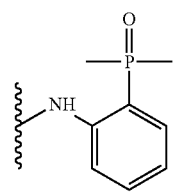

(II)

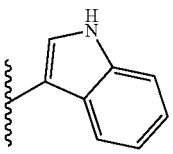

(III)

$R^2$ is $-N(CH_3)_2$, $-NH_2$, or a group represented by the following formula (IV).

[Formula 15]

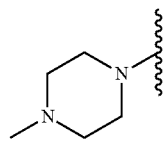

(IV)

This cell growth suppression is induced by the reduced EGFR activity and thus the inhibitor can be a drug effective against a lung cancer having the resistance to the third generation EGFR-TKI.

Additionally, it is conceivable that the drug containing the above compound as an active ingredient provides the same effect not only on the EGFR gene mutation-positive non-small cell lung cancers studied herein but also on a tumor having the same mutation C797S in EGFR.

Further, it is revealed that when the compound and an anti-EGFR antibody are used in combination, a stronger tumor regression effect can be obtained. Any anti-EGFR antibody may be used as long as it inhibits the EGFR activity. Examples of the antibody include necitumumab approved by U.S. Food and Drug Administration (FDA) as a non-small cell lung cancer (squamous cell lung cancer) therapeutic agent, and cetuximab and panitumumab currently used in the therapy for colorectal cancers, but are not limited thereto and any antibody may be used as long as it inhibits the EGFR activity. The currently used antibodies are conceived to bind to the extracellular domain of EGFR and inhibit the binding of the ligand, EGF (Non Patent Literatures 22 to 24). The antibody to be used for the therapy may be any antibodies such as those having an overlapping epitope with these antibodies or those recognizing a different epitope as long as they inhibit the EGFR activity.

As illustrated in the following examples, the cases where the therapeutic agent containing the above compound as an active ingredient is effective are those with a point mutation of cysteine to serine at position 797 in EGFR. Thus, the test for confirming the efficacy of these drugs may be any method as long as it can detect the C797S mutation in EGFR.

The method for detecting mutations of the gene may be any methods as long as they can confirm the sequence at position 797 in EGFR such as PCR-based test methods and direct sequence methods. Additionally, when detecting mutations in EGFR proteins, mutations may be detected by methods such as tissue staining and ELISA using an antibody which specifically recognizes the C797S mutation. For the test subject, any of those may be used as long as they contain tumor cells such as, in addition to tumor tissues, cavity fluids including pleural fluid to begin with, sputum, aspiration phlegm, and blood.

Hereinafter, the present invention is described in reference to data.

1. Effect of Brigatinib on EGFR Mutants

<<EGFR Mutants, and Preparation of Mutant Expressing Cell Lines>>

As described earlier, most of the EGFR gene mutation-positive non-small cell lung cancers are the exon 19 deletion or the L858R mutation, accounting for 80% or more all together of the total. Thus, cell lines having the exon 19 deletion mutation and the L858R point mutation were prepared and analyzed.

Wild type EGFR was obtained from cDNA of an A549 cell line. The EGFR mutants, exon 19 deletion mutant, is amplified by PCR using an HCC827 cell line, and the L858R mutant is amplified by PCR using a specimen of lung cancer, and these mutants are cloned respectively into pENTR vector (Thermo Fisher Scientific) so as to include an activated full length EGFR.

The mutations of T790M and C797S were introduced to each EGFR using the following primers respectively in the form of a single mutation or double mutations by QuikChange Site-Directed Mutagenesis Kit (Agilent).

```
                                        (SEQ ID NO: 1)
T790M F:    CCGTGCAGCTCATCATCCAGCTCATGCCCTTC (SEQ ID NO: 2)
T790M R:    GAAGGGCATGAGCTGCATGATGAGCTGCACGG (SEQ ID NO: 3)
C797S F:    CATGCCCTTCGGCTCCCTCCTGGAGCTA (SEQ ID NO: 4)
C797S R:    TAGTCCAGGAGGGAGCCGAAGGGCATG
```

The obtained EGFR mutants were inserted to a lentiviral vector, pLenti6.3/V5-DEST (Life Technologies), to construct each EGFR mutant. The EGFR mutant was introduced to a mouse pro B cell Ba/F3 using Vira-Power Lentiviral Directional TOPO Expression System (Life Technologies).

<<Effect of Tyrosine Kinase Inhibitors on EGFR Mutant Expressing Cells>>

The screening for agents that inhibit the growth of the cell lines having the C797S mutation was carried out by using, in a Ba/F3 cell, a cell line which has the EGFR exon 19 deletion mutation as in a lung cancer, a cell line wherein the C797S mutation is further introduced (BaF3 C797S/del19), a mutant line wherein T790M, which is the point mutation of threonine to methionine at position 790 appeared as the resistance to a first generation drug, is introduced (BaF3 T790M/del19), and a mutation line wherein the C797S mutation, which is the point mutation of cysteine to serine at position 797 appeared as the resistance to a third generation drug, is further introduced (BaF3 C797S/T790M/del19).

To the above 4 types of Ba/F3 cell mutant lines, 30 types of tyrosine kinase inhibitors were added so as to be a concentration of 100 nM and the effects thereof were analyzed. After 72 hours, the cell viabilities were analyzed using CellTiter-Glo assay (registered trademark, Promega Corporation). The tyrosine kinase inhibitors used and the sources thereof are shown in Table 1.

TABLE 1

| drug | Company | Drug | Company |
|---|---|---|---|
| 17-AAG | LC laboratories | EGF-816 | ChemScene |
| AEW541 | ActiveBiochem | Erlotinib | LC laboratories |
| Afatinib | ChemieTek | Foretinib | AdooQ Bioscience |
| Alectinib | ActiveBiochem | Gefitinib | LC laboratories |
| AP26113-analogue | Sellek | Imatinib | LC laboratories |
| ASP3026 | ChemieTek | Lapatinib | LC laboratories |
| AZD3463 | BioVision | Lorlatinib | ActiveBiochem |
| BGJ398 | Shanghai Biochem | Nintedanib | Selleck |
| Brigatinib | Shanghai Biochem | Osimertinib | Selleck |
| Cabozantinib | ActiveBiochem | PHA665752 | TOCRIS Bioscience |
| CEP701 | Calbiochem | Ponatinib | Selleck |
| Ceritinib | ActiveBiochem | Sorafenib | Selleck |
| CO-1686 | ActiveBiochem | Sunitinib | Selleck |
| Crizotinib | Biochempartner | TAE684 | ChemieTek |
| E7080 | Selleck | Vandetanib | Shanghai Biochem |

Relative viabilities, with those to which DMSO was added as a control, are shown in FIG. 1. Of the inhibitors used for the analysis shown in Table 1, only brigatinib and ponatinib demonstrated an about 50% inhibitory effect at a concentration of 100 nM on C797S/T790M/exon 19 deletion mutant. However, ponatinib also had about the same $IC_{50}$ on the parental line Ba/F3 and is thus presumed not to have the growth inhibitory effect specifically on the EGFR mutant having the C797S mutation.

<<Effect of Brigatinib on C797S/T790M/exon 19 Deletion Mutant Expressing Cells>>

As the results of the above screening, brigatinib was revealed to have the growth suppression effect on the C797S mutant expressing cells. Thus, the cell viabilities were determined by carrying out treatments at different concentrations of gefitinib, afatinib, osimertinib, and were also determined brigatinib which was found to have been effective on the C797S mutation by the present inventors.

Two thousand Ba/F3 mutant cells were seeded in a 96-well plate, and each mutant was treated with 0.3 nM to 10000 nM of gefitinib, afatinib, osimertinib, and brigatinib to analyze the cell viabilities after 72 hours by CellTiter-Glo assay.

Figure 2A:
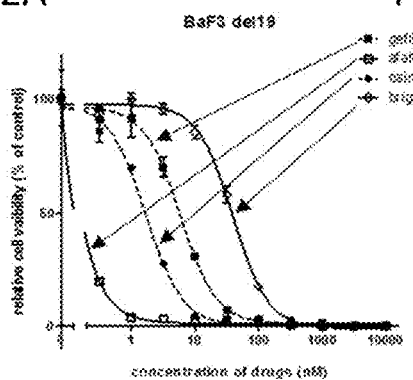
FIG. 2A is a drawing showing the effects of gefitinib, afatinib, osimertinib, and brigatinib on the cell viability against EGFR exon 19 deletion mutant expressing Ba/F3 cells.
Figure 2B:
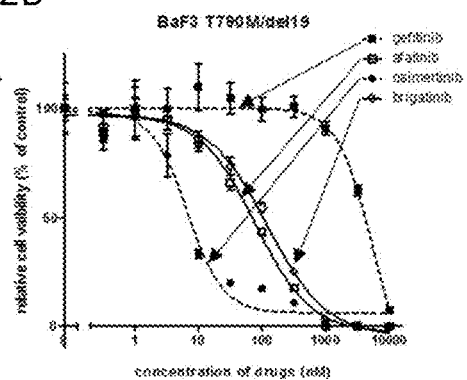
FIG. 2B is a drawing showing the effects of the above compounds on the cell viability against EGFR T790M/exon 19 deletion mutant expressing cells.

FIGS. 2A to D show the cell viability of each mutant cell line by the agent treatment, and Table 2 shows the $IC_{50}$. Afatinib, osimertinib, and gefitinib demonstrated the cell growth suppression effect on the EGFR exon 19 deletion mutation (del19) (FIG. 2A). Further, the Ba/F3 having the T790M mutation in addition to the exon 19 mutation (T790M/del19) demonstrated a high sensitivity with an $IC_{50}$ of 6.7 nM to osimertinib but demonstrated a high resistance with an $IC_{50}$ of 5603 nM to gefitinib (Table 2).

Figure 2C:
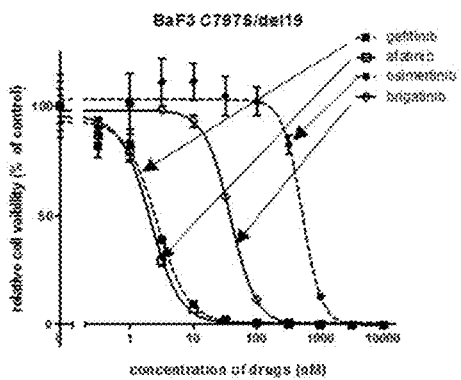
FIG. 2C is a drawing showing the effects of the above compounds on the cell viability against EGFR C797S/exon 19 deletion mutant expressing cells.

Gefitinib and afatinib demonstrated the cell growth suppression on the cell line (C797S/del19) having the point mutation of C797S in addition to the exon 19 deletion mutation in EGFR (FIG. 2C).

Figure 2D:
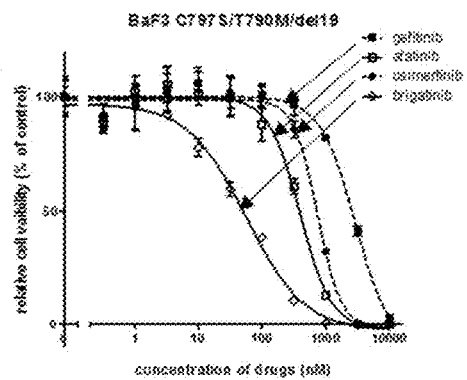
FIG. 2D is a drawing showing the effects of the above compounds on the cell viability against EGFR triple-mutant C797S/T790M/exon 19 deletion mutant expressing cells.

On the other hand, neither of gefitinib, afatinib, or osimertinib, even when treated at high concentrations, suppressed the growth against the triple-mutant expressing cell line having point mutations at 2 positions 797 and 790 in addition to the exon 19 deletion mutation in EGFR (C797S/T790M/del19), whereas brigatinib suppressed the cell growth at a low concentration of an $IC_{50}$ 67.2 nM (FIG. 2D, Table 2). More specifically, brigatinib effectively works on the cell having the C797S mutation, in addition to the exon 19 deletion mutation and the T790M mutation.

TABLE 2

| IC$_{50}$(nM) | gefitinib | afatinib | osimertinib | brigatinib |
|---|---|---|---|---|
| del19 | 5.9 | <0.3 | 1.7 | 43.7 |
| T790M/del19 | 5603 | 78.2 | 6.7 | 150.3 |
| C797S/del19 | 2.7 | 2.1 | 513.4 | 39.9 |
| C797S/T790M/del19 | 2922 | 392.7 | 740.5 | 67.2 |

Figure 2E:
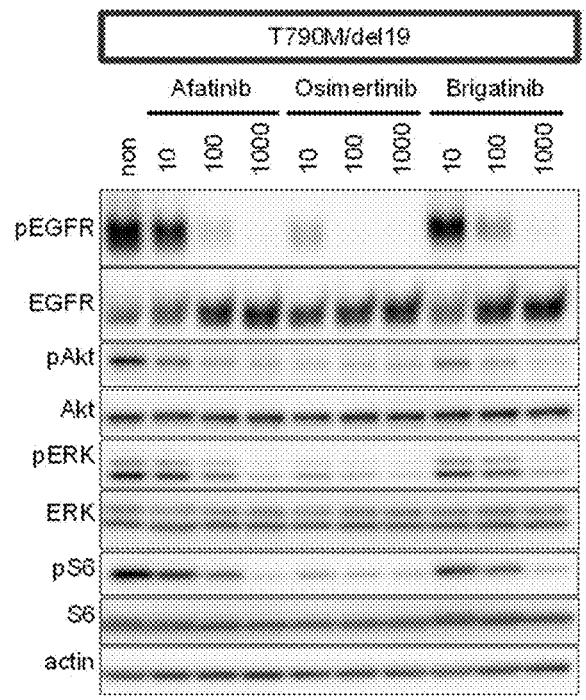
FIG. 2E is a drawing showing the analysis on the phosphorylation of the EGFR signal transduction pathway molecules of EGFR T790M/exon 19 deletion mutant expressing Ba/F3 cells treated with afatinib, osimertinib, or brigatinib.

Subsequently, the phosphorylation of EGFR and the downstream signal transductions when the T790M/del19 and the C797S/T790M/del19 cell lines were treated with 10, 100, 1000 nM of afatinib, osimertinib, and brigatinib were analyzed by Western blotting (FIGS. 2E and F).

Each protein was detected using anti-phospho-EGFR antibody (Tyr1068, Abcam, ab5644), anti-EGFR antibody (Cell Signaling Technology, #4267), anti-phospho-Akt antibody (Ser473, Cell Signaling Technology, #4060), anti-Akt antibody (Cell Signaling Technology, #4691), anti-phospho-ERK antibody (Thr202/Tyr204, Cell Signaling Technology, #9101), anti-ERK1/2 antibody (Cell Signaling Technology, #9102), anti-phospho-S6 antibody (Ser240/244, Cell Signaling Technology, #5364), anti-S6 antibody (Cell Signaling Technology, #2217), and anti-β-actin antibody (Sigma-Aldrich, A5228).

Figure 2F:
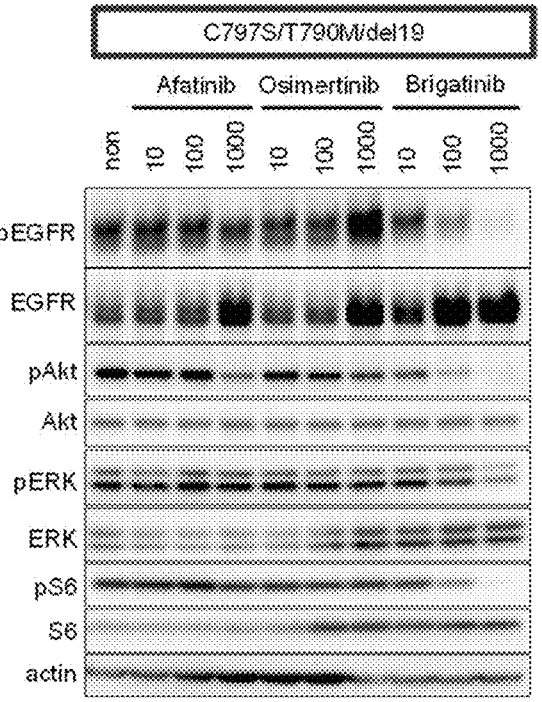
FIG. 2F is a drawing showing the analysis on the phosphorylation of the EGFR signal transduction pathway molecules of EGFR triple-mutant C797S/T790M/exon 19 deletion mutant expressing cells treated with afatinib, osimertinib, or brigatinib.

The results obtained by using the T790M/del19 cells are shown in FIG. 2E and the results obtained by using the C797S/T790M/del19 cells are shown in FIG. 2F. Osimertinib strongly suppressed the phosphorylation of EGFR in the T790M/del19 Ba/F3 cells but did not suppress the phosphorylation of EGFR at all in the C797S/T790M/del19 Ba/F3 cells. Further, afatinib, when treated at 100 nM, was confirmed to have suppressed the phosphorylation of EGFR in the T790M/del19 Ba/F3 cells but was not confirmed at all to have suppressed the phosphorylation in the C797S/T790M/del19 Ba/F3 cells. In contrast, brigatinib suppressed the phosphorylation of EGFR and the downstream signal in both cells. Particularly, in the C797S/T790M/del19 cell, the decrease in the phosphorylation of EGFR and the downstream signal transductions Akt, ERK, and S6 were confirmed only with brigatinib. Note that, gefitinib, while not shown here, demonstrated the same effect as afatinib on the phosphorylation of the EGFR signal transductions.

<<Effect of Brigatinib on C797S/T790M/L858R Mutant Expressing Cells>>

In lung cancers, the point mutation L858R wherein leucine, the amino acid at position 858 in EGFR, is substituted with arginine is found equivalently the amino acid deletion mutation in the EGFR exon 19. Thus, the effect of each agent on the L858R mutation was analyzed.

The effects of gefitinib, afatinib, osimertinib, and brigatinib were analyzed using Ba/F3 wherein leucine at position 858 is mutated to arginine (BaF3 L858R), Ba/F3 having duplicated mutations of the T790M mutation and the L858R mutation (BaF3 T790M/L858R), Ba/F3 having duplicated mutations of C797S and L858R (BaF3 C797S/L858R), and Ba/F3 having the above three mutations (BaF3 C797S/T790M/L858R). Ba/F3 mutation lines were prepared in the same manner as above to determine the cell viabilities by CellTiter-Glo assay. The results are shown in FIG. 3 and Table 3.

Afatinib, gefitinib, and osimertinib inhibit the growth of the cells having the point mutation of L858R.

Figure 3A:
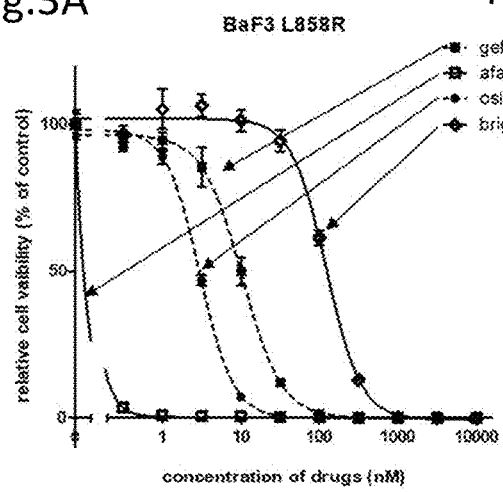
FIG. 3A is a drawing showing the effects of gefitinib, afatinib, osimertinib, and brigatinib on the cell viability against an EGFR L858R mutant expressing Ba/F3 cells.
Figure 3B:
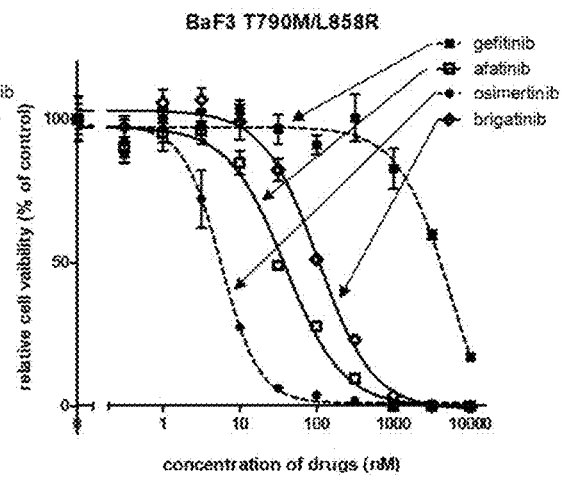
FIG. 3B is a drawing showing the effects of the above compounds on the cell viability against EGFR T790M/L858R mutant expressing cells.
Figure 3C:
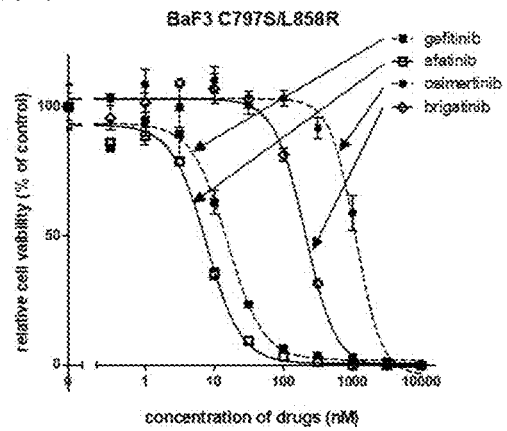
FIG. 3C is a drawing showing the effects of the above compounds on the cell viability against EGFR C797S/L858R mutant expressing cells.
Figure 3D:
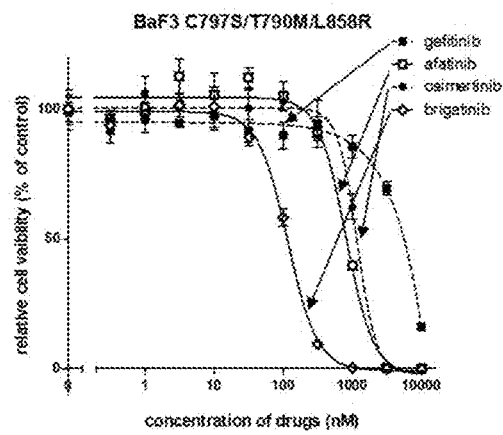
FIG. 3D is a drawing showing the effects of the above compounds on the cell viability against EGFR triple-mutant C797S/T790M/L858R mutant expressing cells.
Figure 4A:
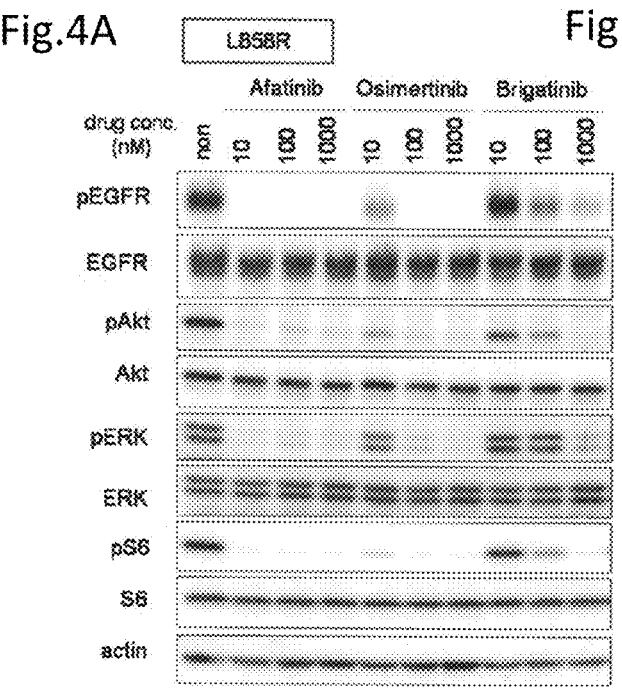
FIG. 4A is a drawing showing the analysis on the phosphorylation of the EGFR signal transduction pathway molecules of EGFR L858R mutant expressing Ba/F3 cells treated with afatinib, osimertinib, and brigatinib.
Figure 4B:
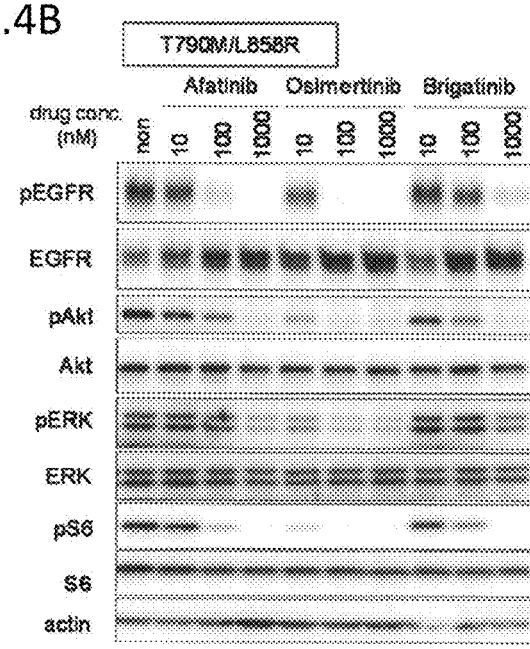
FIG. 4B is a drawing showing the analysis on the phosphorylation of the EGFR signal transduction pathway molecules of EGFR T790M/L858R mutant expressing cells treated with the above compounds.
Figure 4C:
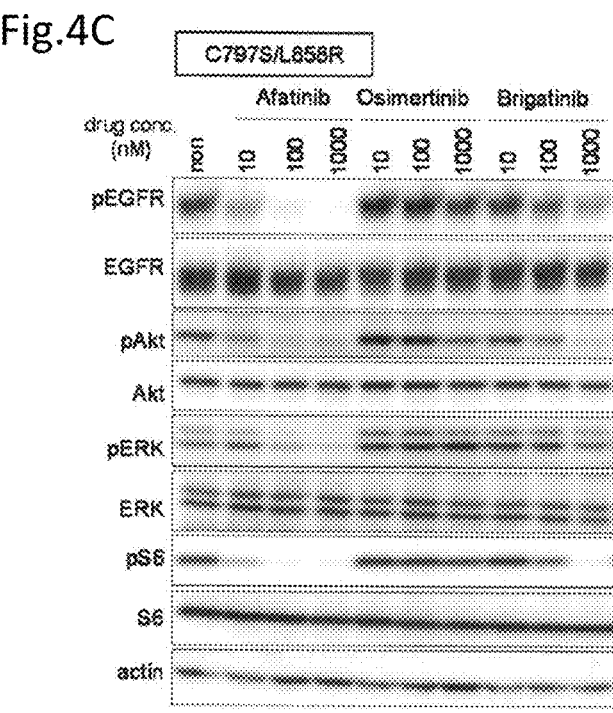
FIG. 4C is a drawing showing the analysis on the phosphorylation of EGFR signal transduction pathway molecules of EGFR C797S/L858R mutant expressing cells treated with the above compounds.
Figure 4D:
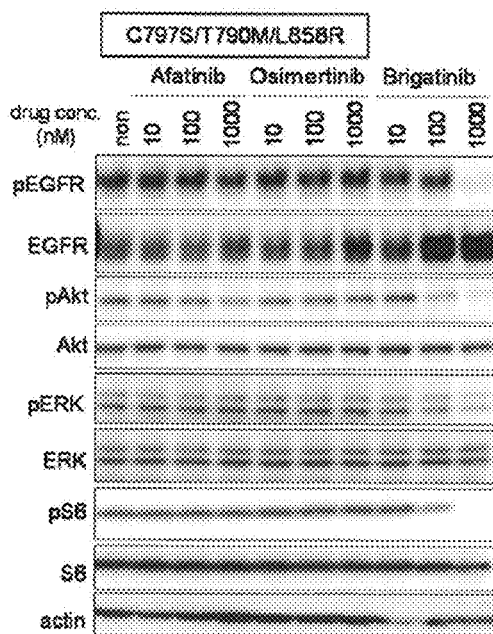
FIG. 4D is a drawing showing the analysis on the phosphorylation of the EGFR signal transduction pathway molecules of EGFR triple-mutant C797S/T790M/L858R mutant expressing cells treated with the above compounds.

Particularly, afatinib was found to have an extremely strong cell growth suppression effect on the L858R mutant lines. On the other hand, brigatinib had a low cell growth suppression effect on the cells having the point mutation of L858R (FIG. 3A). Further, osimertinib provides a strong cell growth suppression effect on the cell having duplicated mutations of T790M/L858R (IC$_{50}$ 5.8 nM), whereas afatinib has an IC$_{50}$ of 39.2 nM and gefitinib has an IC$_{50}$ of 5922 nM demonstrating substantially no effect. Brigatinib demonstrates a significant cell growth suppression effect compared to gefitinib, but the effect thereof is much weaker compared to osimertinib (FIG. 3B). Furthermore, only afatinib (IC$_{50}$ 7.7 nM) and gefitinib (IC$_{50}$ 15.5 nM) demonstrate the effects on the duplicated mutations of C797S/L858R, osimertinib demonstrates substantially no cell growth suppression effect, brigatinib demonstrates a significant cell growth suppression effect compared to osimertinib but the effect thereof is weaker compared to afatinib and gefitinib (FIG. 3C). On the other hand, brigatinib has a notable cell growth suppression effect (IC$_{50}$ 161.5 nM) on Ba/F3 cell having three mutations of C797S/T790M/L858R, whereas osimertinib (IC$_{50}$ 1171 nM), afatinib (IC$_{50}$ 804.2 nM), and gefitinib (IC$_{50}$>10000 nM) demonstrate substantially no effects (FIG. 3D).

TABLE 3

| IC$_{50}$(nM) | gefitinib | afatinib | osimertinib | brigatinib |
|---|---|---|---|---|
| L858R | 10.4 | <0.3 | 3.0 | 207.0 |
| T790M/L858R | 5922 | 39.2 | 5.8 | 1651 |
| C790S/L858R | 15.5 | 7.7 | 1115 | 297.6 |
| C797S/T790M/L858R | >10000 | 804.2 | 1171 | 161.5 |

Next, using the above four types of cell lines having the L858R mutation, the phosphorylation of EGFR and the downstream signal transductions were analyzed (FIGS. 4A to D). Afatinib strongly suppressed the phosphorylation of EGFR and the downstream signal transductions in the L858R mutant expressing cells, had a somewhat weaker effect in the C797S/L858R mutant expressing cells, and was confirmed to have an extremely weak suppression effect in T790M/L858R but was not substantially confirmed to have a suppression effect in the C797S/T790M/L858R mutant expressing cells.

Osimertinib is confirmed to have a suppression effect, despite being weaker than afatinib, on the phosphorylation of the signal transductions in the L858R mutant expressing cells and have the strongest suppression effect in the T790M/L858R mutant expressing cells. On the other hand, osimertinib was not substantially confirmed to have the phosphorylation suppression effect in the C797S/L858R mutant expressing cells or the C797S/T790M/L858R mutant expressing cells.

Brigatinib was confirmed to have a phosphorylation suppression effect to some extent on the EGFR signal transductions in the L858R, T790M/L858R, and C797S/L858R mutants expressing cells. Further, brigatinib was the only compound confirmed to have the effect of suppressing the phosphorylation of the EGFR signal transductions in the C797S/T790M/L858R mutant expressing cells. This result is well consistent with the results of the cell viabilities shown in FIGS. 3, whereby brigatinib is conceived to suppress the cell growth via the EGFR signal transductions.

In view of the above results, brigatinib is conceived to have the cell growth suppression effect on the activated EGFR having duplicated point mutations of C797S/T790M. Additionally, brigatinib has the same effect of suppressing the cell growth whether the mutation of EGFR for activation, which is responsible for cancer, is the exon 19 deletion mutation or the point mutation L858R. Note that gefitinib, while not shown here, demonstrated the same effect, despite being weaker than afatinib, on the phosphorylation of the EGFR signal transductions.

2. Effect of ALK Inhibitors on EGFR Mutants

<<Search for Other ALK Inhibitors Providing the Effect on Triple Mutants>>

Figure 5:
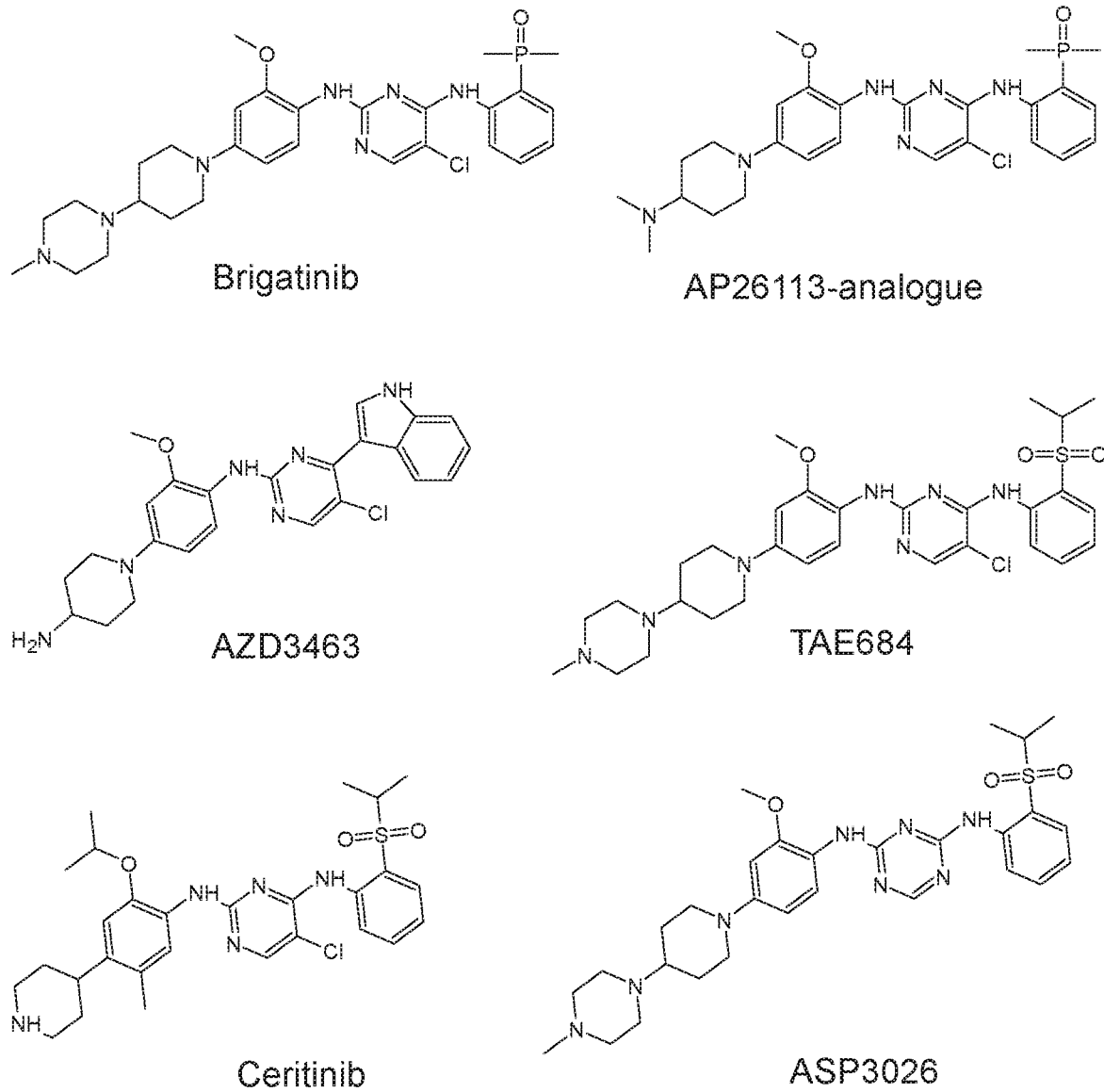
FIG. 5 is a drawing showing the structures of ALK inhibitors.

Brigatinib is an ALK inhibitor, and hence other ALK inhibitors were analyzed to see if they have the same effect as brigatinib. The analyzed ALK inhibitors are 6 compounds which are, in addition to brigatinib, AP26113-analog which is an analog thereof, AZD3463, TAE684, LDK378 (ceritinib), and ASP3026 (FIG. 5).

First, using the cell lines wherein the exon 19 deletion mutant (del19), T790M/del19 (T/D), C797S/del19 (C/D), or C797S/T790M/del19 (C/T/D) mutants are introduced to Ba/F3, the cell viabilities were analyzed. The results are shown in FIGS. 6A to D and Table 4.

TABLE 4

| IC50 (nM) | brigatinib | AP26113-analogue | AZD3463 | TAE684 | ceritinib | ASP3026 |
|---|---|---|---|---|---|---|
| Del19 | 43.7 | 36.9 | 90.0 | 314.4 | 524.3 | 450.1 |
| T/D | 150.3 | 138.6 | 175.4 | 540.0 | 1007 | 2165 |
| C/D | 39.9 | 28.4 | 74.4 | 229.3 | 576.6 | 323.9 |
| C/T/D | 67.2 | 59.1 | 131.5 | 340.7 | 780.5 | 1508 |

Brigatinib, AP26113-analog, and AZD3463 demonstrated strong cell growth suppression effects on the Ba/F3 to which the EGFR mutant having any of the mutations is introduced. Particularly, brigatinib and AP26113-analog demonstrated extremely strong growth suppression effects on the C797S/T790M/del19 mutants, respectively with $IC_{50}$ 67.2 nM and $IC_{50}$ 59.1 nM.

Then, the cell lines wherein the mutant of L858R (L858R), T790M/L858R (T/L), C797S/L858R (C/L), or C797S/T790M/L858R (C/T/L) was introduced to Ba/F3 were also analyzed for the cell viabilities (FIGS. 7A to D and Table 5).

TABLE 5

| IC50 (nM) | brigatinib | AP26113-analogue | AZD3463 | TAE684 | ceritinib | ASP3026 |
|---|---|---|---|---|---|---|
| L858R | 132.9 | 92.1 | 287.3 | 528.7 | 1164 | 947.6 |
| T/L | 53.7 | 36.0 | 184.5 | 232.6 | 685.2 | 1691 |
| C/L | 188.3 | 107.9 | 374.5 | 524.1 | 1043 | 1041 |
| C/T/L | 116.8 | 69.2 | 167.5 | 355.9 | 1020 | 2148 |

Figure 6A:
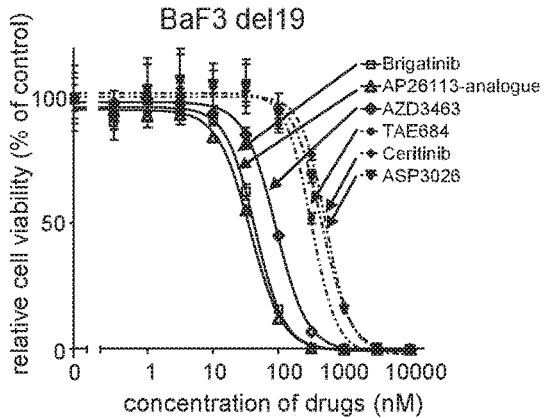
FIG. 6A is a drawing showing the effects of ALK inhibitors, brigatinib, AP26113-analog, AZD3463, TAE684, ceritinib, and ASP3026 on the cell viability against EGFR exon 19 deletion mutant expressing Ba/F3 cells.
Figure 6B:
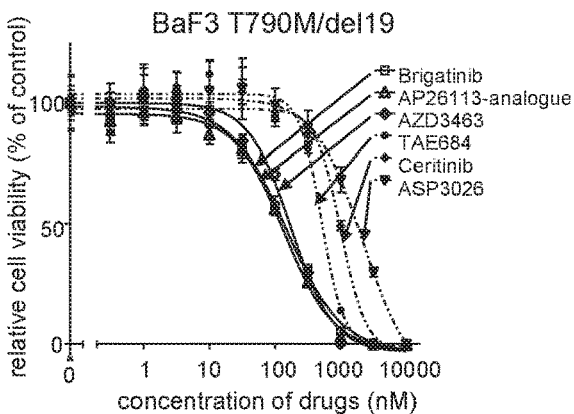
FIG. 6B is a drawing showing the effects of the above ALK inhibitors on the cell viability against EGFR T790M/exon 19 deletion mutant expressing cells.
Figure 6C:
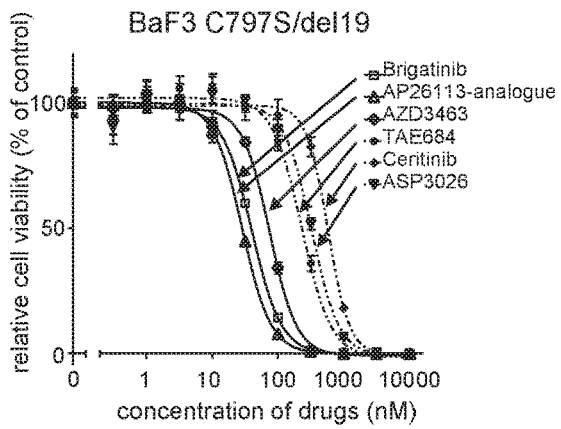
FIG. 6C is a drawing showing the effects of the above ALK inhibitors on the cell viability against EGFR C797S/exon 19 deletion mutant expressing cells.
Figure 6D:
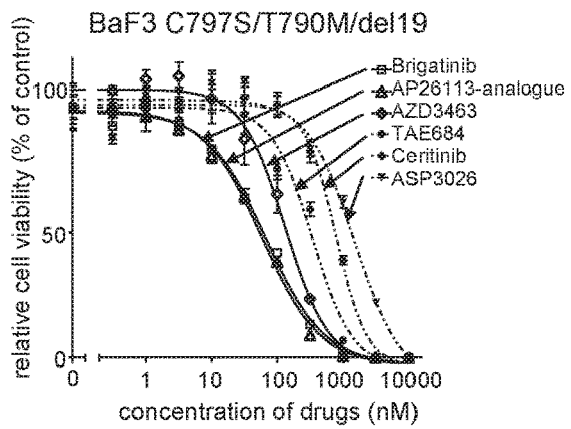
FIG. 6D is a drawing showing the effects of the above ALK inhibitors on the cell viabilities against EGFR triple-mutant C797S/T790M/exon 19 deletion mutant expressing cells.
Figure 7A:
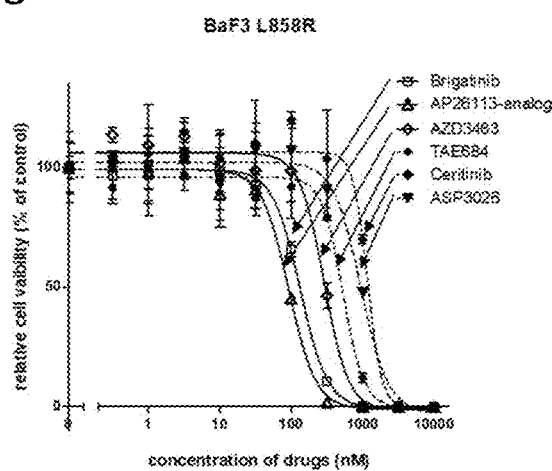
FIG. 7A is a drawing showing the effects of the above ALK inhibitors on the cell viability against EGFR L858R mutant expressing Ba/F3 cells.
Figure 7B:
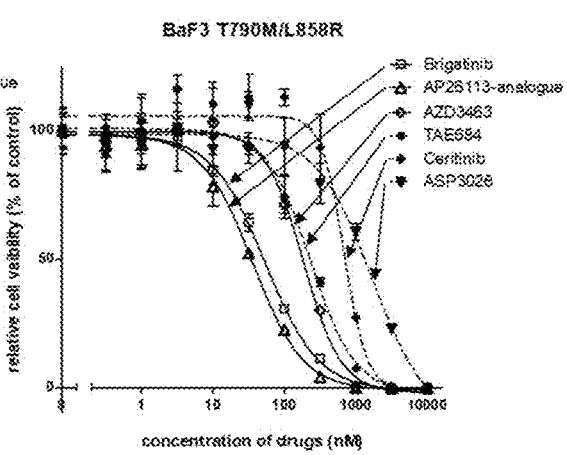
FIG. 7B is a drawing showing the effects of the above ALK inhibitors on the cell viability against EGFR T790M/L858R mutant expressing cells.
Figure 7C:
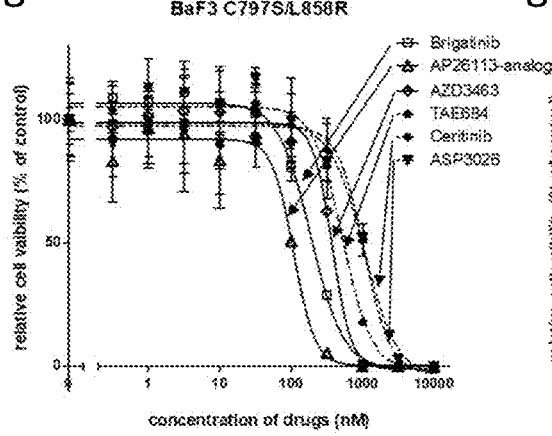
FIG. 7C is a drawing showing the effects of the above ALK inhibitors on the cell viability against an EGFR C797S/L858R mutant expressing cells.
Figure 7D:
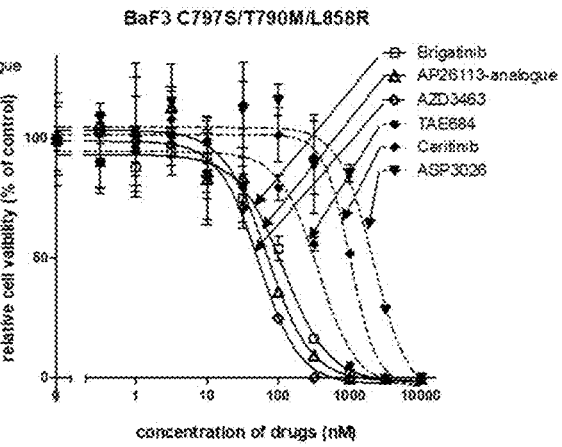
FIG. 7D is a drawing showing the effects of the above ALK inhibitors on the cell viability against EGFR triple-mutant C797S/T790M/L858R mutant expressing cells.

Brigatinib, AP26113-analog, and AZD3463 demonstrated strong cell growth suppression effects on the Ba/F3 to which the EGFR mutant having any of the mutations is introduced. Brigatinib demonstrated a strong cell growth suppression effect on the EGFR mutant expressing cells having the L858R along with the C797S mutation and the T790M mutation in combination (FIG. 7D). On the other hand, the EGFR mutant expressing cells having the exon 19 deletion mutation had a slightly reduced cell growth suppression effect in the case with only the T790M mutation but had a strong cell growth suppression effect in the case with the C797S mutation alone or with both C797S and T790M (triple mutations). There were differences between the mutants on cell growth suppression effect (FIGS. 6B to D). However, brigatinib, AP26113-analog, and AZD3463 provide the same effect in having strong cell growth suppression effects on the EGFR mutation cell line having the C797S mutation in addition to T790M.

Further, TAE684, ceritinib, and ASP3026 did not substantially demonstrate the cell growth suppression effect on the EGFR mutant expressing cells despite being the same ALK inhibitors. The six compounds beginning with brigatinib shown in FIG. 5 have the same basic skeletons and are extremely analogous compounds. However, the effects on the EGFR mutants were revealed to have been different.

In view of the analysis results on the ALK inhibitors, the compound represented by the following general formula (I) is conceived to have the effect on the EGFR having the C797S mutation.

[Formula 16]

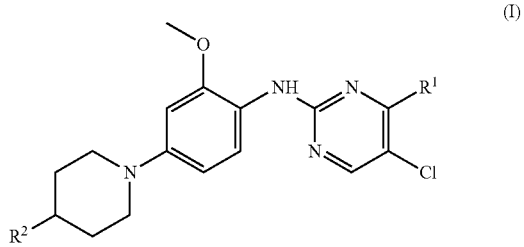

wherein $R^1$ is a group represented by the following formula (II) or (III)

[Formula 17]

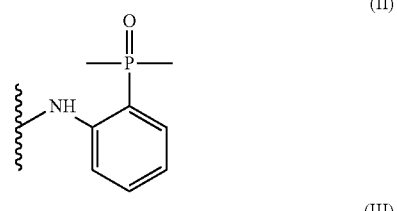

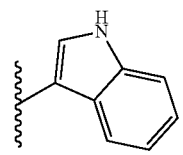

$R^2$ is —N(CH$_3$)$_2$, —NH$_2$, or a group represented by the following formula (IV)

[Formula 18]

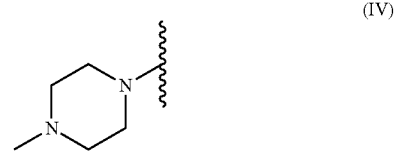

These compounds have the equal skeleton to brigatinib, AP26113-analog, and AZD3463, and thus are conceived to demonstrate the same effect as brigatinib or the like on the EGFR mutants.

Figure 8A:
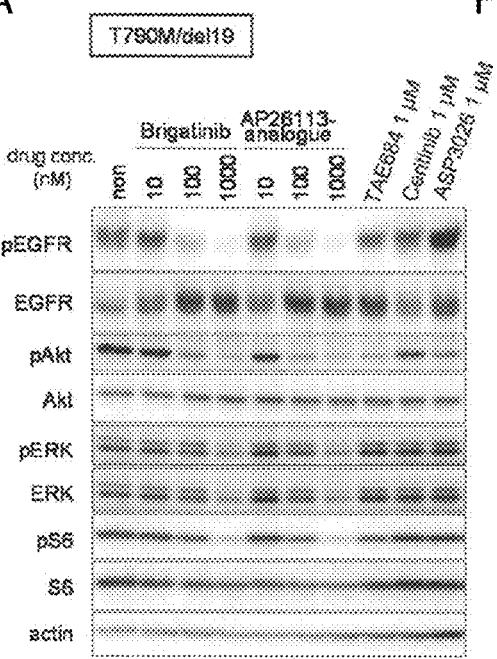
FIG. 8A is a drawing showing the analysis on the phosphorylation of the EGFR signal transduction pathway molecules of EGFR T790M/exon 19 deletion mutant expressing Ba/F3 cells treated with ALK inhibitors brigatinib, AP26113-analog, TAE684, ceritinib, and ASP3026.
Figure 8B:
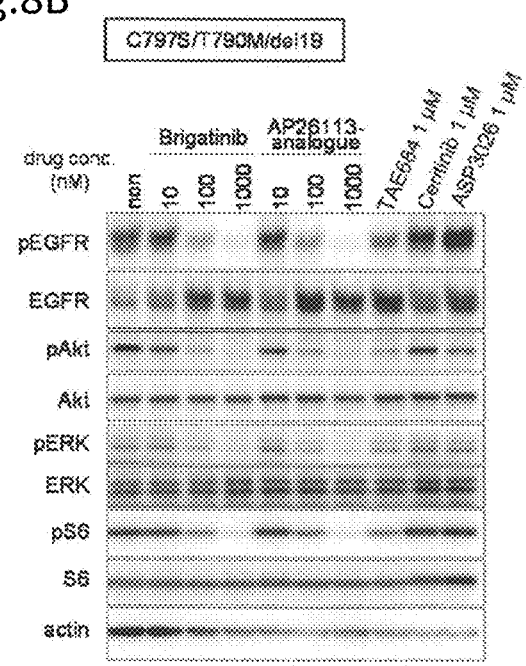
FIG. 8B is a drawing showing the analysis on the phosphorylation of the EGFR signal transduction pathway molecules of EGFR triple-mutant C797S/T790M/exon 19 deletion mutant expressing cells treated with the above ALK inhibitors.
Figure 8C:
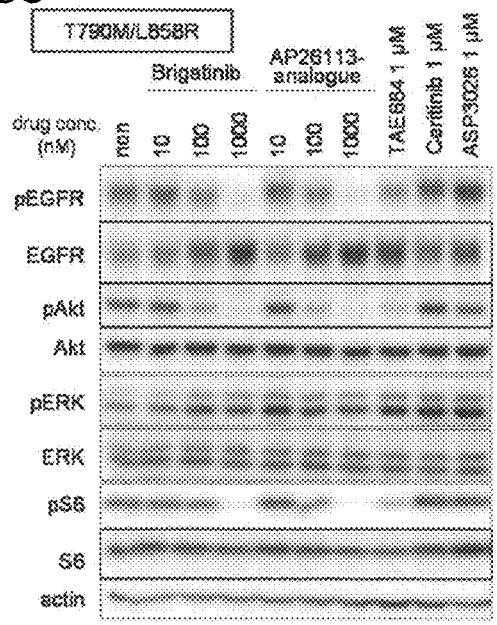
FIG. 8C is a drawing showing the analysis on the phosphorylation of the EGFR signal transduction pathway molecules of EGFR T790M/L858R mutant expressing cells treated with the above ALK inhibitors.
Figure 8D:
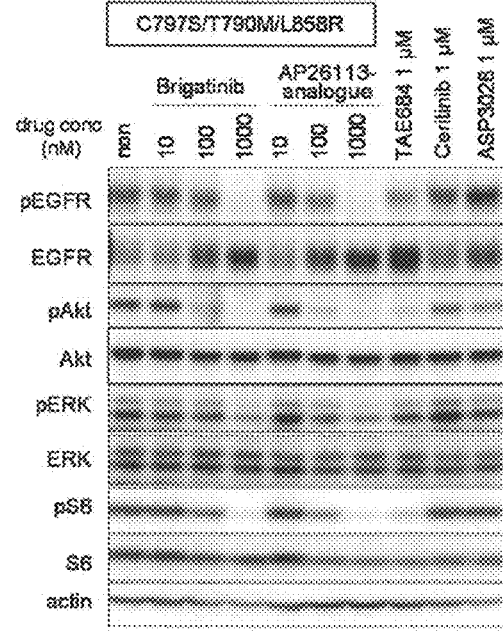
FIG. 8D is a drawing showing the analysis on the phosphorylation of the EGFR signal transduction pathway molecules of EGFR triple-mutant C797S/T790M/L858R mutant expressing cells treated with the above ALK inhibitors.

Subsequently, each of the compounds was analyzed for the suppression effect on the phosphorylation of EGFR and the downstream signal transductions of EGFR (FIGS. 8A to D). The analysis was carried out using the EGFR mutants expressing cells whose parental cell line is Ba/F3, having the exon 19 deletion as a basal mutation (FIGS. 8A and 8B) and the EGFR mutants expressing cells having the L858R as a basal mutation (FIGS. 8C and 8D). As in the effect on the cell viability, brigatinib and AP26113-analog, which is an analog thereof, demonstrated the inhibitory activity against the EGFR signal transductions. Particularly, strong suppression effects are demonstrated in the case where the C797S and T790M mutations are used in combination. On the other hand, TAE684, ceritinib, and ASP3026 did not substantially demonstrate the inhibitory effect on the EGFR signal transductions even when treated at a high concentration of 1 μM.

<<Analysis Using Human Lung Cancer-Derived Cell Line PC9>>

The Ba/F3 cells used in the analysis so far are the mouse pro B cell-derived line, and thus the analysis was carried out using PC9 which is a human lung cancer-derived cell line, to see if the same effects can be obtained. The cell line PC9 is a human non-small cell lung cancer-derived cell line having the EGFR exon 19 deletion mutation. Using PC9, EGFR mutants expressing cells were prepared in the same manner, then analyze the effects of these compounds (FIG. 9). Cells expressing EGFR having, in addition to the exon 19 deletion, further mutations T790M and C797S/T790M were prepared in PC9 (del19), which was the parental line, and gefitinib, osimertinib, and brigatinib were added in different concentrations from 0.3 nM to 10000 nM to thereby determine the cell viabilities after 72 hours in the same manner by CellTiter-Glo assay.

Figure 9A:
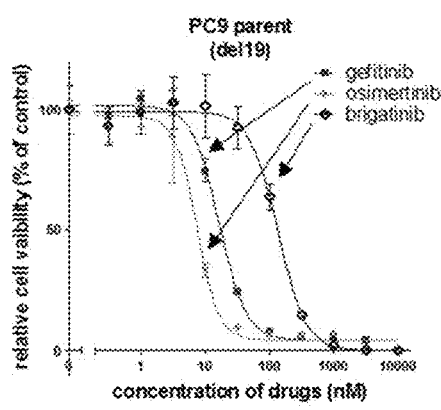
FIG. 9A is a drawing showing the effects of gefitinib, osimertinib, and brigatinib on the cell viability against a human lung cancer cell line PC9 (EGFR exon 19 deletion mutant).
Figure 9B:
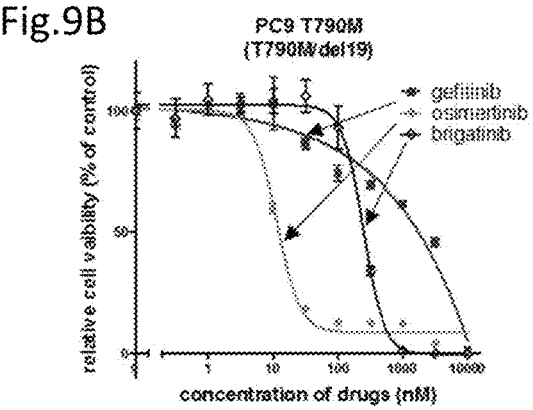
FIG. 9B is a drawing showing the effects of the above compounds on the cell viability against a T790M/exon 19 deletion mutant expressing PC9 cell line.
Figure 9C:
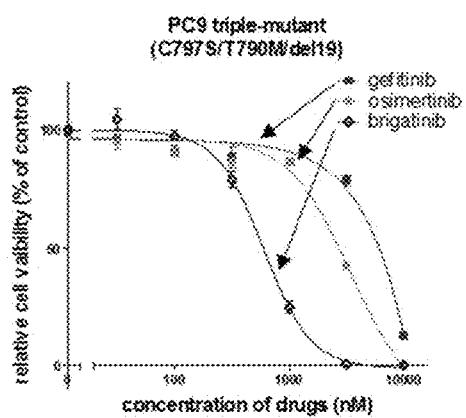
FIG. 9C is a drawing showing the effects of the above compounds on the cell viability against a triple-mutant C797S/T790M/exon 19 deletion mutant expressing PC9 cell line.

As in the EGFR mutants prepared with the Ba/F3 parent line, gefitinib and osimertinib demonstrated the cell growth suppression effects on the parent line PC9 (exon 19 deletion mutation), whereas brigatinib only demonstrated an extremely weak cell growth suppression effect (FIG. 9A). Osimertinib demonstrated an extremely strong cell growth suppression effect in the cell line wherein the T790M mutation was introduced to PC9 (T790M/del19), whereas brigatinib demonstrated a weak cell growth suppression effect and gefitinib did not substantially demonstrate the cell growth suppression effect (FIG. 9B). Further, brigatinib demonstrated the cell growth suppression effect on the triple mutants having the C797S mutation (C797S/T790M/del19), whereas gefitinib and osimertinib did not substantially demonstrate the cell growth suppression effect even when treated at high concentrations (FIG. 9C).

Then, PC9 and the cell lines having PC9 as the parental line are treated with various tyrosine kinase inhibitors to analyze the phosphorylation of EGFR and the downstream signal transductions by western blotting, and the results of which are shown (FIG. 10). Afatinib very strongly, and osimertinib and gefitinib also very strongly suppressed the phosphorylation of EGFR and the downstream signal transductions thereof in the parental line PC9. On the other hand, brigatinib and AP26113-analog demonstrated the suppressing effect on the activation of the EGFR signal transductions but the effect was weaker compared to afatinib (FIG. 10A).

Figure 10A:
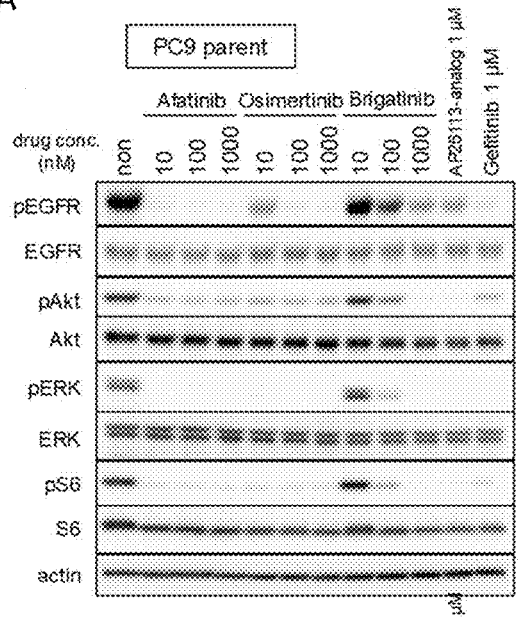
FIG. 10A is a drawing showing the analysis on the phosphorylation of the EGFR signal transduction pathway molecules in a PC9 cell line treated with various tyrosine kinase inhibitors.
Figure 10B:
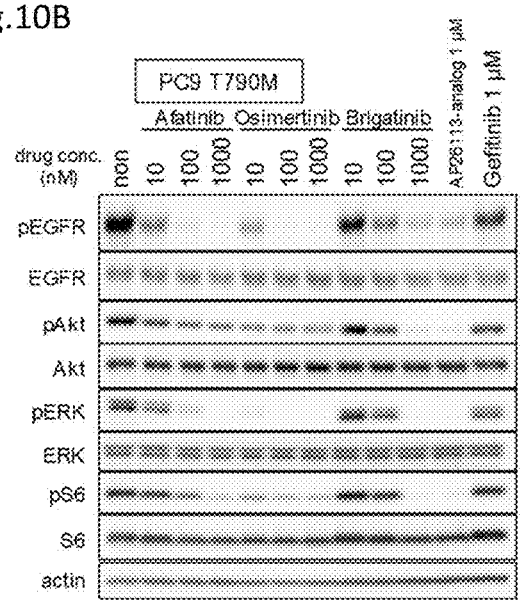
FIG. 10B is a drawing showing the analysis on the phosphorylation of the EGFR signal transduction pathway molecules in a T790M/exon 19 deletion mutant expressing PC9 cell line treated with various tyrosine kinase inhibitors.

In the cell line wherein T790M was introduced to PC9, osimertinib, afatinib, and brigatinib, in this order, demonstrated the effects of suppressing the phosphorylation of EGFR and the downstream signal transductions thereof. Further, AP26113-analog demonstrated the equal suppression effect to brigatinib but gefitinib did not substantially demonstrate the phosphorylation suppression effect (FIG. 10B).

Figure 10C:
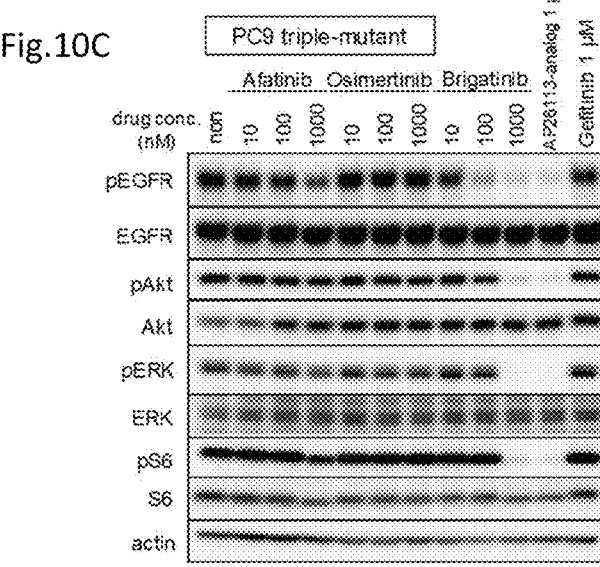
FIG. 10C is a drawing showing the analysis on the phosphorylation of the EGFR signal transduction pathway molecules in a triple-mutant expressing PC9 cell line treated with various tyrosine kinase inhibitors.
Figure 10D:
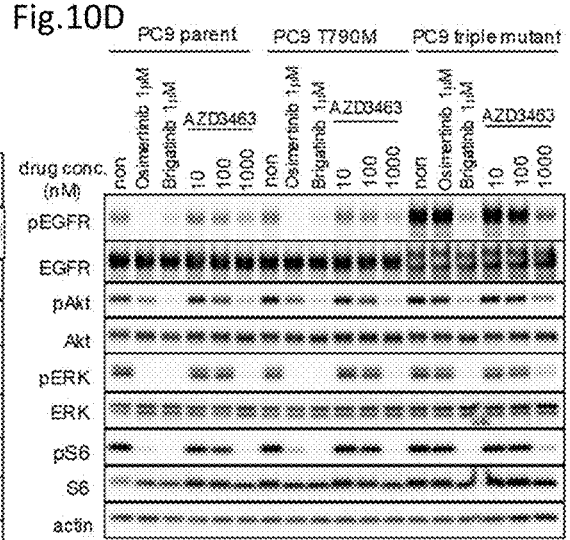
FIG. 10D is a drawing showing the analysis on the phosphorylation of the EGFR signal transduction pathway molecules in PC9 and mutants treated with AZD3463.
Figure 11A:
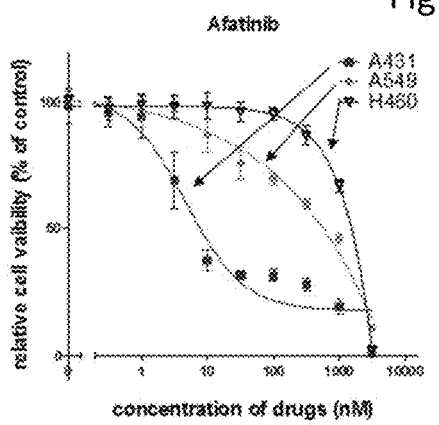
FIG. 11A is a drawing showing the effect of afatinib on EGFR mutation free cell lines.
Figure 11B:
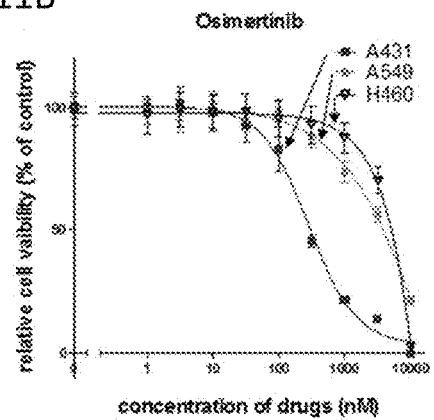
FIG. 11B is a drawing showing the effect of osimertinib on EGFR mutation free cell lines.
Figure 11C:
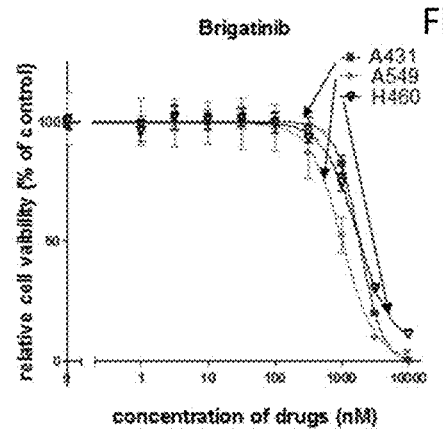
FIG. 11C is a drawing showing the effect of brigatinib on EGFR mutation free cell lines.
Figure 11D:
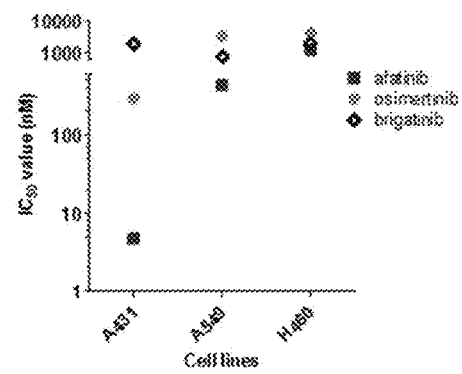
FIG. 11D is a drawing collectively showing the effects of afatinib, osimertinib, and brigatinib on each of the cell lines.

Brigatinib and AP26113-analog demonstrated the suppression effects on the phosphorylation of EGFR and the downstream signal transductions in the triple-mutant of PC9, whereas neither of afatinib, osimertinib, or gefitinib demonstrated the suppression effect on the phosphorylation of EGFR (FIG. 10C). Further, AZD3463 was also analyzed for the effect on these mutants (FIG. 10D). AZD3463, as in the case with brigatinib and AP26113-analog, had the effect of suppressing the phosphorylation of the EGFR signal transductions in the triple-mutant expressing cells in PC9 with C797S mutation. Furthermore, AZD3463 was also confirmed to have the effect of suppressing the phosphorylation of EGFR and the downstream signal transductions thereof in the parental line PC9 and in the EGFR mutant expressing cells which T790M was further introduced to PC9.

In view of the above results, it was demonstrated that brigatinib, AP26113-analog, and AZD3463 also provide the same effects as the results obtained in the Ba/F3 even in PC9, which is a human lung cancer cell.

<<Effect of Tyrosine Kinase Inhibitors on Wild Type EGFR Expressing Cells>>

The effect of brigatinib on the cell growth was analyzed using cell lines having mutations other than the point mutation and deletion mutation in EGFR. The analysis was carried out using A431 wherein EGFR is amplified and A549 and H460 which have a mutation at K-ras. A431 is a cell line derived from a human epithelioid cell cancer and A549 and H460 are cell lines derived from human lung cancers. Note that, EGFR has no mutations despite A431 being amplified, and EGFR also has no mutations in A549 and H460.

Afatinib and osimertinib suppress the cell growth against A431 wherein EGFR is amplified. Further, in the cell line having a mutation at K-ras, afatinib demonstrates a weak cell growth suppression effect on A549 but others did not substantially demonstrate the suppression effect on the cell growth. On the other hand, brigatinib did not demonstrate the cell growth suppression effect on any of the cell lines. This suggests that brigatinib does not suppress the cell growth against the wild type EGFR, more specifically, brigatinib targets only cancer cells and does not suppress the growth of normal cells.

3. Effect of Brigatinib In Vivo

<<Study Using Mice Transplanted with EGFR Mutants Expressing Ba/F3>>

The analysis was carried out to see if the effect of brigatinib on EGFR having the mutation at C797S demonstrated in the experiment using the cultured cell lines is similarly obtained in vivo.

Figure 12A:
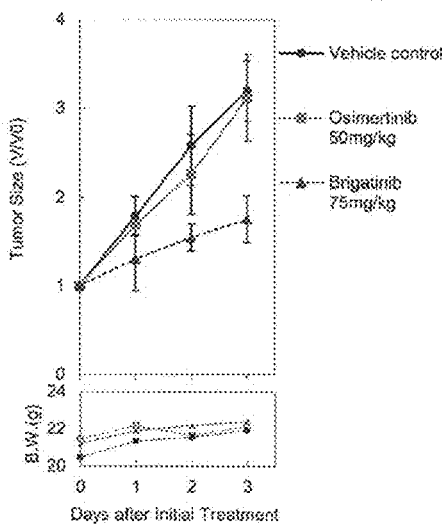
FIG. 12A is a drawing showing the effects of brigatinib and osimertinib on mice transplanted with Ba/F3 having the triple-mutant C797S/T790M/exon 19 deletion mutation in EGFR.
Figure 12B:
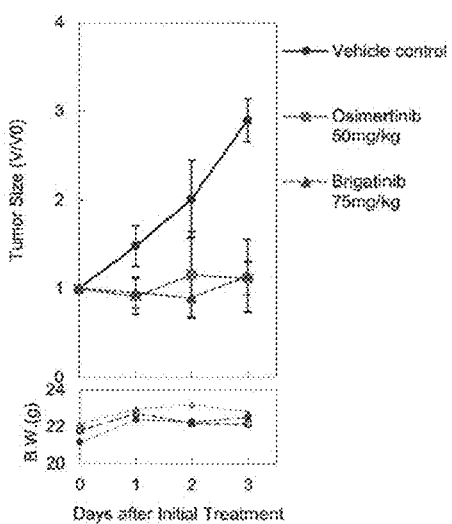
FIG. 12B is a drawing showing the effects of brigatinib and osimertinib on mice transplanted with Ba/F3 having the T790M/exon 19 deletion mutation in EGFR.

Ba/F3 cells in a density of $2 \times 10^6$ expressing the C797S/T790M/del19 mutant or the T790M/del19 mutant were suspended in 50 μl of HBSS and subcutaneously transplanted into SCID mice. The growth of tumor cells was measured for the tumor width and length using a caliper twice weekly to determine the volume by calculation ($0.5 \times$ length×width×width ($mm^3$)). After the tumor reached the size of 100 $mm^3$, the mice were randomly divided into 3 groups of solvent only, 50 mg/kg osimertinib, and 75 mg/kg brigatinib, and forced oral administration was carried out once daily. When the tumor volume on the day of starting administration is set to 1, the change in the post administration tumor volume was calculated. FIG. 12A shows the results of transplantation of the C797S/T790M/del19 mutant expressing cells and FIG. 12B shows the results of transplantation of the T790M/del19 mutant expressing cells.

As in the experiment results using the cultured cells, brigatinib had a strong growth suppression effect on C797S/T790M/del19, which has the C797S and T790M mutations in combination (FIG. 12A). Further, the growth suppression effect on T790M/del19 was also confirmed (FIG. 12B). Osimertinib had the effect on T790M/del19 but did not substantially demonstrate the suppression effect on C797S/T790M/del19.

In view of the above results, it was revealed that brigatinib has the effect not only on the cultured cells but also on the EGFR mutations having the C797S and T790M mutations in combination in vivo.

<<Study Using Mice Transplanted with EGFR Mutants Expressing PC9>>

Figure 13A:
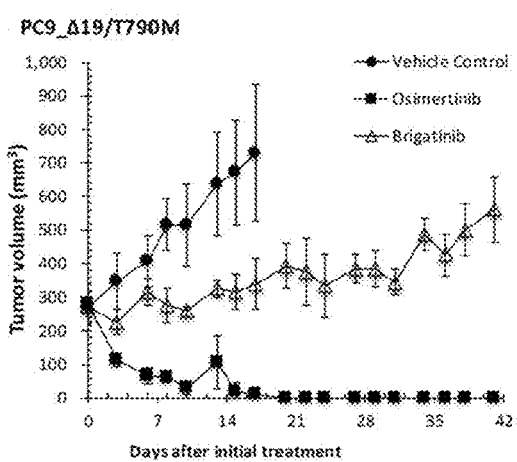
FIG. 13A is a drawing showing the effects of brigatinib and osimertinib on mice transplanted with a T790M/exon 19 deletion mutant expressing PC9 cell line.

The confirmation on the in vivo effect of brigatinib was carried out in the same manner using the cell lines having PC9 as the parental line (FIG. 13). EGFR T790M/exon19 deletion mutant expressing PC9 cells were subcutaneously transplanted into Balb-c nu/nu mice, after the tumor volume reached an average of 200 mm$^3$, the mice were randomly divided into 3 groups of 5 mice each of solvent only, 50 mg/kg osimertinib, and 75 mg/kg brigatinib, and forced oral administration was carried out once daily. The tumor volume was measured in the same manner as above. Osimertinib demonstrated a notable effect on the tumor growth. Brigatinib did not demonstrate the effect as notable as osimertinib but an apparent tumor growth suppression effect was found compared to the group to which only the solvent was administered (FIG. 13A).

Figure 13C:
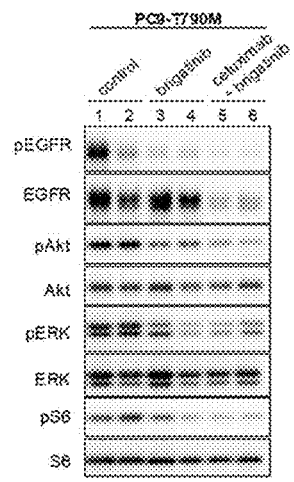
FIG. 13C is a drawing showing the analysis of xenograft tumor on the phosphorylation of the EGFR signal transduction pathway molecules from brigatinib or the brigatinib and cetuximab combination treated mice transplanted EGFR-T790M/exon19 deletion mutant expressing PC9 cells.
Figure 13B:
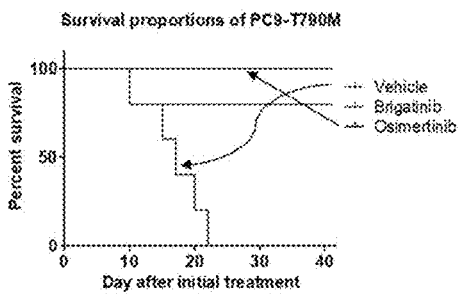
FIG. 13B is a drawing showing the survival curves of the above mice.

The survival curves based on the Kaplan-Meier method were shown in FIG. 13B. Both of the osimertinib administered group and the brigatinib administered group into which T790M expressing PC9 was transplanted were alive during the observation period. Note that 1 mouse in the brigatinib treated group died by mistake on day 10 at the time of oral administration.

The study was carried out on the protein phosphorylation of EGFR and the downstream signal transductions thereof in the tumor transplanted into the mice (FIG. 13C). After transplanting the tumor in the same manner as above, the administration was carried out with the solvent only, 75 mg/kg brigatinib, and cetuximab (Merck) at a dose of 1 mg/mouse 3 times weekly in addition to 75 mg/kg brigatinib, and the tumors were removed after 10 days to analyze by Western blotting. The results are shown from 2 mice per group. In the brigatinib administered group, all had the suppressed phosphorylation of EGFR and the downstream signal transductions thereof compared to the control group to which only the solvent was administered. Further, in the group where cetuximab was used in combination, a stronger effect was obtained compared to the group administered with brigatinib singly (FIG. 13C).

Figure 14A:
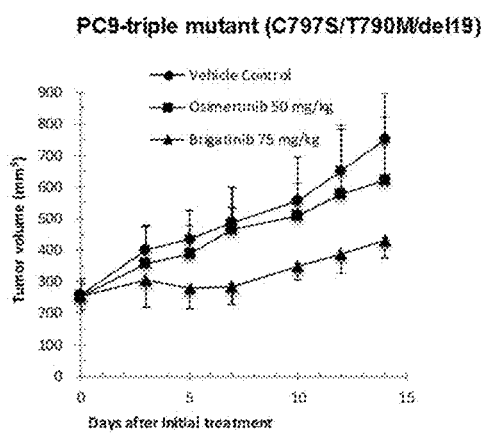
FIG. 14A is a drawing showing the effects of brigatinib and osimertinib on mice transplanted with a triple-mutant expressing PC9 cell line.
Figure 14B:
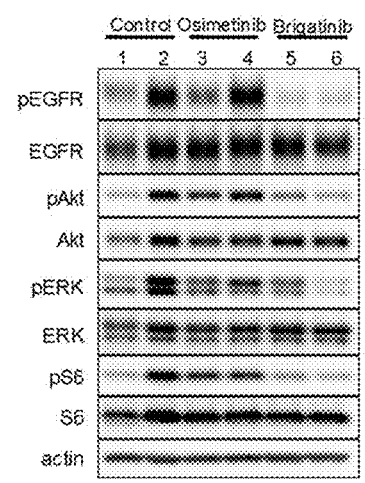
FIG. 14B is a drawing showing the analysis on the phosphorylation of the EGFR signal transduction pathway molecules from osimertinib and brigatinib treated mice xenograft tumor transplanted with triple mutant expressing cells.

Next, using the cells expressing EGFR C797S/T790M/del19 mutations in PC9 and transplanted into Balb-c nu/nu in the same manner as above to study the effects of osimertinib and brigatinib (FIG. 14). Osimertinib was not substantially effective on the EGFR triple mutations, whereas brigatinib demonstrated a significant growth suppression effect on the tumor growth (FIG. 14A). EGFR and the downstream signal transductions in the post-transplantation tumor into the mice were analyzed by Western blotting in the same manner as above. As a result, brigatinib demonstrated an apparent suppression effect on the phosphorylation of EGFR and the downstream signal transductions, whereas the phosphorylation suppression effect was not substantially found in the osimertinib administered group (FIG. 14B).

4. Combination Effect with an Anti-EGFR Antibody

<<Effect of Use in Combination with Cetuximab>>

Anti-EGFR antibodies suppress the EGFR phosphorylation and are thus known to be effective against a constantly activated tumor having an EGFR mutation. The effect of brigatinib was analyzed on the synergistic effect with an anti-EGFR antibody.

As studied above, brigatinib demonstrates the growth suppression effect on the cell growth in low concentrations against PC9 wherein EGFR having the C797S/T790M/del19 mutations was expressed, whereas osimertinib did not demonstrate the effect on the cell growth unless treated in a high concentration (see FIG. 9C). Treatment was carried out with cetuximab in combination with brigatinib or osimertinib to study the effect on the cell growth (FIG. 15A).

Brigatinib or osimertinib in a concentration of 300 nM and cetuximab in a concentration of 10 μg/ml were added to a culture solution of PC9 wherein EGFR having the C797S/T790M/del19 mutations was expressed and, the cell viabilities were analyzed 72 hours after in the same manner as above using CellTiter-Glo assay. Cetuximab in a concentration of 10 μg/ml did not demonstrate the effect on the cell growth. On the other hand, brigatinib, when treated in a concentration of 300 nM, demonstrated the suppression effect on the cell growth even used singly but provided a suppression effect as strong as about 50% in the cell viability when added in combination with cetuximab. In contrast, osimertinib did not provide the effect on the cell growth even when used in combination with cetuximab.

PC9 wherein EGFR having the C797S/T790M/del19 mutations was expressed was treated with brigatinib in a concentration range of 0 to 1000 nM in the presence or absence of cetuximab and the phosphorylation of EGFR and the downstream signal transductions was analyzed by Western blotting (FIG. 15B). In the cells treated with cetuximab and brigatinib in combination, the protein phosphorylation of EGFR and the downstream signal transductions was suppressed more strongly than brigatinib used singly. Particularly, a much stronger signal suppression effect was found in the downstream signal transductions of EGFR.

PC9 expressing EGFR having triple mutations was transplanted into mice in the same manner as above, and the solvent only, brigatinib singly, osimertinib singly, cetuximab singly, and brigatinib and cetuximab in combination were administered to study the growth of tumor cells by the tumor volume (FIG. 15C). Forced oral administration was carried out once daily with brigatinib at a dose of 75 mg/kg and osimertinib at a dose of 50 mg/kg, and cetuximab was administered at a dose of 1 mg/mouse 3 times weekly. Compared to the control group to which only the solvent was administered, the tumor growth suppression effects to some extent were found in the groups administered with brigatinib singly, osimertinib singly, and cetuximab singly but an apparent tumor growth suppression effect was found in the group to which brigatinib and cetuximab were administered in combination where gradual tumor regression was observed (FIG. 15C).

The phosphorylation of EGFR and the downstream signal transductions thereof in the post-transplantation tumor into the mice was analyzed by Western blotting in the same manner as above (FIG. 15D). In response to the results shown in FIG. 15C, the phosphorylation of EGFR and the downstream signal transductions thereof was notably suppressed in the tumor obtained from the group to which brigatinib and cetuximab were administered in combination.

The survival curves based on the Kaplan-Meier method was shown in FIG. 15E. When PC9 wherein EGFR having triple mutations is expressed was transplanted, no substantial effect was found with osimertinib single administration but brigatinib single administration and cetuximab single administration had life-extension effects to some extent. In contrast, all the mice were alive during the 60-day observation period in the group to which brigatinib and cetuximab were administered in combination. Thus, it is desirable to administer brigatinib and cetuximab in combination to the tumor expressing EGFR having triple mutations.

Figure 16A:
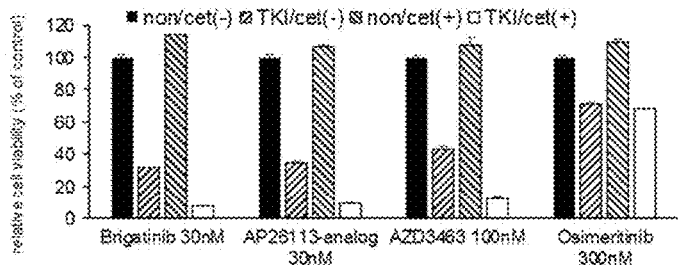
FIG. 16A is a drawing of the study on the combination effect of cetuximab and tyrosine kinase inhibitors on the cell viability of a triple-mutant expressing Ba/F3 cell line.

Then, using the cells expressing the C797S/T790M/del19 EGFR mutations in Ba/F3 and cells were analyzed on the combination effect with an anti-EGFR antibody (FIG. 16). The cells were cultured in 30 nM of brigatinib, 30 nM of AP26113-analog, 100 nM of AZD3463, or 300 nM of osimertinib in the presence or absence of 10 µg/ml cetuximab, and the cell viabilities after 72 hours was evaluated using CellTiter-Glo assay.

Brigatinib, AP26113-analog, AZD3463, and osimertinib demonstrate the effect of reducing the cell viability even used singly but cetuximab in a concentration of 10 µg/ml when used singly did not demonstrate the effect of reducing the cell viability. Although the effect was not found with cetuximab used singly at a concentration of 10 µg/ml, a stronger effect on the cell viability was found when used in combination with brigatinib, AP26113-analog, or AZD3463. On the other hand, the combination effect with cetuximab was not observed with osimertinib.

Figure 16B:
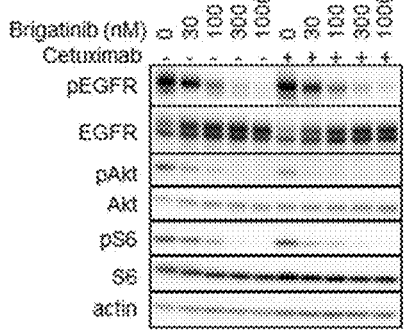
FIG. 16B is a drawing showing the analysis on the effects of brigatinib and cetuximab on the EGFR signal transductions of the above triple-mutant cell line.

The cells expressing C797S/T790M/del19 mutations in Ba/F3 were treated with brigatinib in a concentration range of 0 to 1000 nM in the presence or absence of cetuximab and the phosphorylation of EGFR and the downstream signal transductions was analyzed by Western blotting (FIG. 16B). The cells treated with cetuximab and brigatinib in combination demonstrated a stronger signal suppression effect than brigatinib used singly. Particularly, a much stronger signal suppression effect was found in the EGFR downstream signal transductions.

<<Effect of Use in Combination with Panitumumab>>

Figure 17A:
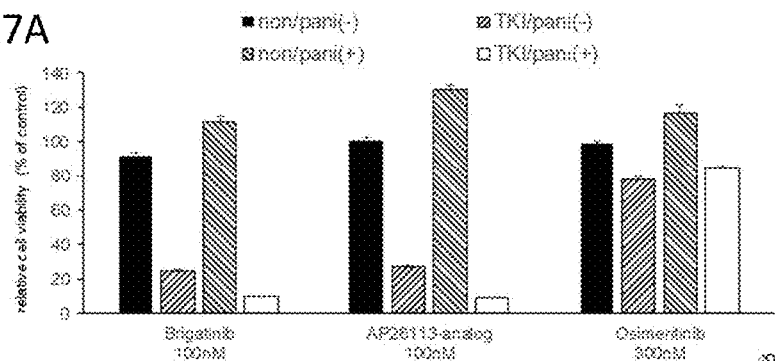
FIG. 17A is a drawing of the study on the combination effect of panitumumab and tyrosine kinase inhibitors on the cell viability of a triple-mutant expressing Ba/F3 cell line.

For confirming that the combination effect with brigatinib or the like is not distinctive to cetuximab, the same analysis was carried out using other anti-EGFR antibody which inhibits the EGFR activity (FIG. 17). To the culture medium of the Ba/F3 cell wherein EGFR having the C797S/T790M/del19 mutations was expressed, 100 nM of brigatinib, 100 nM of AP26113-analog, or 300 nM of osimertinib was added in the presence or absence of 20 µg/ml of panitumumab (Panitumumab, Takeda Pharmaceutical Co., Ltd.), and the cell viabilities were evaluated after 72 hours using CellTiter-Glo assay. As in the results obtained by the study with cetuximab, panitumumab used singly in a concentration of 20 µg/ml does not provide the effect on the cell viability but when used in combination with brigatinib or AP26113-analog, notable decrease in the cell viability was found. Further, the combination effect with panitumumab was not found on osimertinib (FIG. 17A).

Figure 17B:
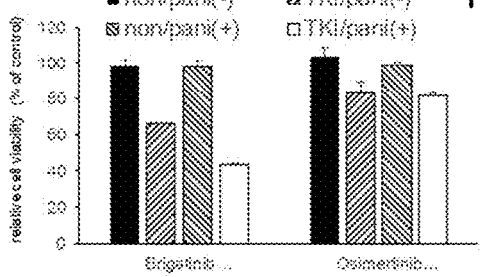
FIG. 17B is a drawing of the study on the combination effect of panitumumab and brigatinib or osimertinib on the cell viability of a triple-mutant expressing PC9 cell line.

The cell wherein the PC9 cell was caused to express EGFR having the C797S/T790M/del19 mutations also studied on the effect of panitumumab in the same manner. A concentration of 300 nM of brigatinib or 300 nM of osimertinib was added to the culture medium, in which the cell was cultured in the presence or absence of 20 µg/ml panitumumab, and the cell viability was evaluated in the same manner after 72 hours. As in the Ba/F3 cell wherein EGFR triple-mutant is expressed, the combination effect with panitumumab was found on brigatinib but the combination effect was not found on osimertinib (FIG. 17B).

Figure 17C:
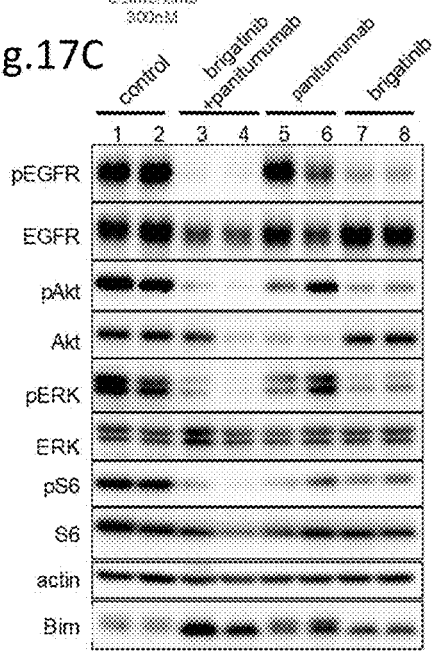
FIG. 17C is a drawing showing the analysis on the effects of panitumumab and brigatinib on the EGFR signal transductions in mice transplanted with a triple-mutant expressing PC9 cell line.

The effects of panitumumab and brigatinib on the EGFR signal transductions in the mice transplanted with PC9 expressing EGFR triple-mutant were analyzed by Western blotting. PC9 expressing EGFR triple-mutant was transplanted into the mice, forced oral administration was carried out with 75 mg/kg of brigatinib once daily and intraperitoneal administration was carried out with panitumumab at a dose of 0.5 mg/mouse twice weekly, and 8 days later the tumors were removed from 2 mice per group and analyzed by Western blotting. The suppression effects on the activation of the EGFR signal transductions are found with brigatinib used singly and panitumumab used singly but, in the group where brigatinib and panitumumab were administered, the activation of the EGFR signal transductions was notably suppressed (FIG. 17C).

The combination effect of brigatinib and an anti-EGFR antibody was studied in mice transplanted with PC9 expressing EGFR triple-mutant. PC9 expressing EGFR triple mutations was transplanted, after the tumor volume reached 200 to 300 mm$^3$, 5 mice each was administered with the solvent only, brigatinib singly, panitumumab singly, the combination of brigatinib and cetuximab, and the combination of brigatinib and panitumumab, and the tumor volumes and the viabilities were analyzed.

Figure 18A:
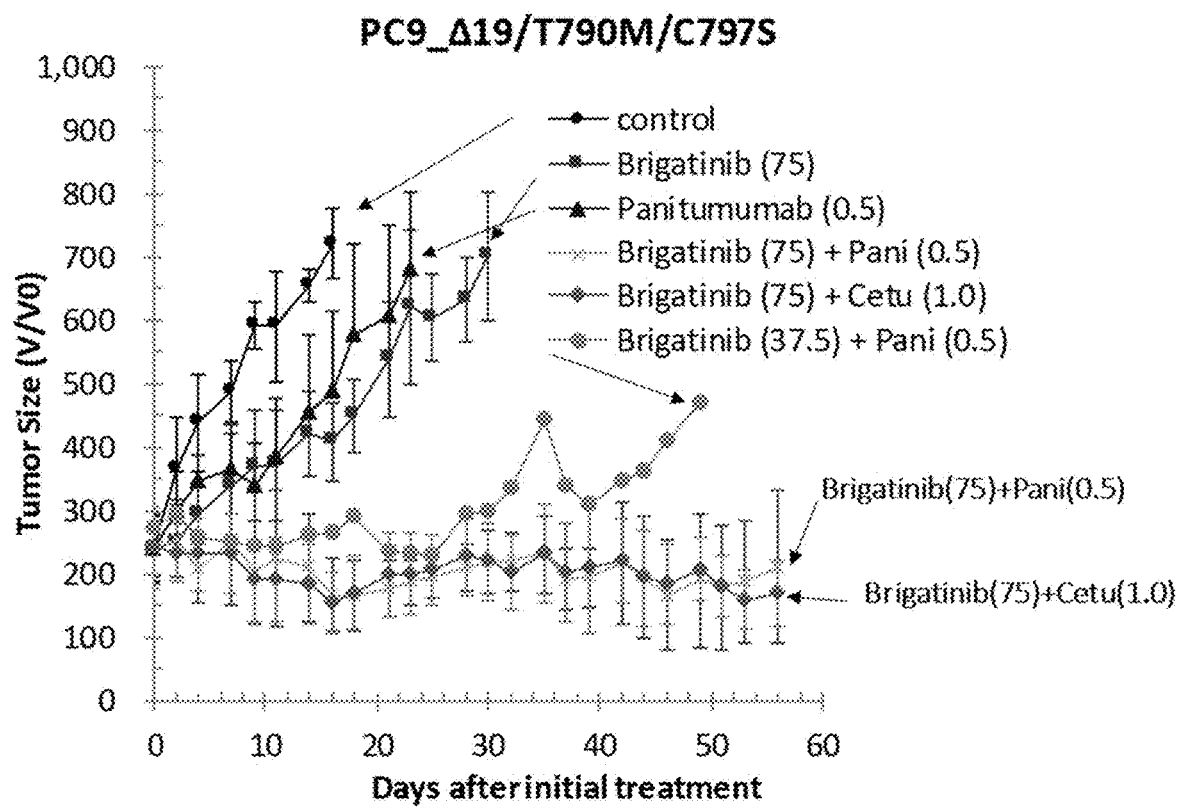
FIG. 18A is a drawing showing the effects of brigatinib, panitumumab, and the combination administration thereof on mice transplanted with a triple-mutant expressing PC9 cell line.
Figure 18A:
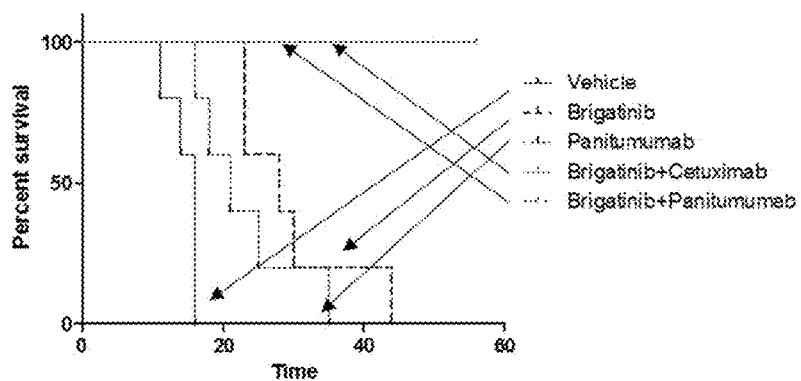
Figure 19:
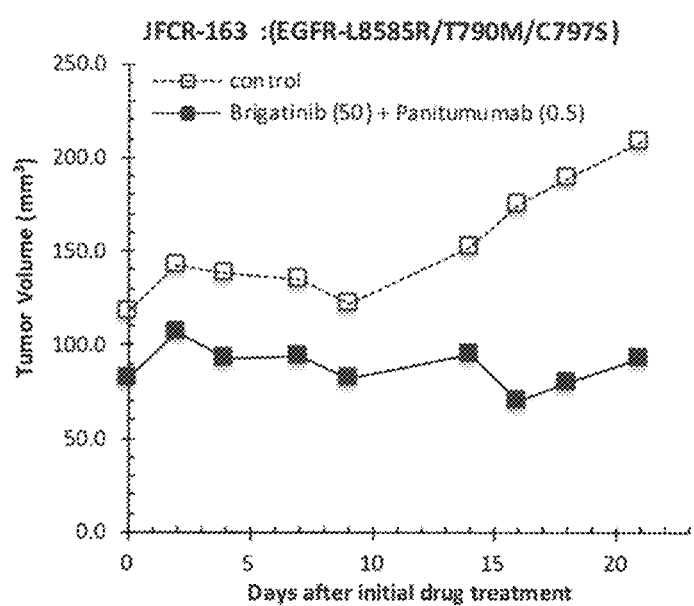
FIG. 19 is a drawing showing the effect of the combination administration of brigatinib and panitumumab on mice transplanted with JFCR-163 (L858R/T790M/C797S triple-mutant line).

Forced oral administration was carried out once daily with brigatinib at a dose of 75 mg/kg or 37.5 mg/kg, and intraperitoneal administration was carried out with panitumumab at a dose of 0.5 mg/mouse and cetuximab at a dose of 1 mg/mouse twice weekly, and the tumor volumes and the cell viabilities were analyzed over time (FIG. 18). Note that 37.5 mg/kg of the brigatinib administration in a mouse corresponds to a dose slightly lower than the dosage in human.

As in the case of analysis using cetuximab above, the suppression effect on the tumor growth to some extent is obtained with panitumumab even used singly compared to the solvent administered control group, but the complete tumor suppression effect cannot be obtained. On the other hand, in the case of administering brigatinib and an anti-EGFR antibody, panitumumab or cetuximab, in combination, the results were obtained that not only the tumor growth suppression but also the gradual tumor regression (FIG. 18A).

In the analytical results on the survival curves by the Kaplan-Meier method, all the mice were alive up to about day 60 in the case where brigatinib and panitumumab or cetuximab were administered in combination. On the other hand, in the brigatinib singly and panitumumab singly administered groups, all the mice were alive for a longer period than the control but died at around day 40.

Further, the combination effect of brigatinib and panitumumab was analyzed using a cell line established from a human lung cancer cell. JFCR-163 Cell line is the cell line established in Japanese Foundation for Cancer Research from the pleural fluid of a patient unresponsive to osimertinib and has EGFR triple mutations (L858R/T790M/C797S). JFCR-163 Cell were transplanted into 2 each of Balb-c nu/nu mice in the same manner as above, after the tumor volume reached about 100 mm$^3$, the mice were randomly divided into 2 groups, with one of which being the treated group and the other being the control group to which only the solvent was administered. For the treated group, forced oral administration was carried out once daily with brigatinib at a dose of 50 mg/kg and intraperitoneal administration was carried out once weekly with panitumumab at a dose of 0.5 mg/kg. As a result of measuring the tumor volume over time, increases in the tumor volume were confirmed in the control group to which only the solvent was administered but the increase in the tumor volume was not confirmed in the group to which brigatinib and panitumumab were administered in combination.

The effect of the combination administration of brigatinib and an anti-EGFR antibody was confirmed regardless of triple mutations having the L858R mutation as basal mutation or triple mutations having the exon 19 deletion as a basal mutation. The result has the crucial meaning in the therapy for lung cancers which have acquired the resistance by the occurrence of a mutation at C797S due to a third generation EGFR-TKI.

In view of these results, it was demonstrated that a stronger therapeutic effect can be obtained by using brigatinib or a compound having the same skeleton with an anti-EGFR antibody in combination on the EGFR mutant having the C797S mutation, i.e., the third mutation, in addition to cancer causative mutation, the EGFR exon 19 deletion or the L858R mutation, and T790M, i.e., the second mutation. Also, as a result of examination of cetuximab and panitumumab as anti-EGFR antibodies, they were found to have a similar effect as long as they can control the binding of the ligand.

As described above, the compounds represented by the general formula (I) represented by brigatinib, AP26113-analog, and AZD3463, have the growth suppression effect on the EGFR mutant having the mutation at C797S of the tumors which have become EGFR-TKI resistant. Further, when the compound is used in combination with an anti-EGFR antibody such as cetuximab or panitumumab, a stronger effect can be obtained. Thus, in EGFR gene mutation-positive non-small lung cancers, the compound has a potential to be an effective therapeutic agent against the third generation EGFR-TKI resistant tumor, for which there is no effective therapeutic method available at present.

The invention claimed is:

1. A therapeutic agent for an EGFR gene mutations-positive non-small cell lung cancer, comprising, in combination:
   brigatinib, AP26113-analog, or AZD3463 as an active ingredient; and
   an anti-EGFR antibody,
   wherein the EGFR gene mutations-positive non-small cell lung cancer is a cancer having a mutation at position 797 of EGFR.

2. The therapeutic agent according to claim 1, wherein the non-small cell lung cancer is a cancer having mutations at positions 797 and 790 of EGFR.

3. The therapeutic agent according to claim 1, wherein the anti-EGFR antibody is cetuximab, panitumumab, or necitumumab.

4. The therapeutic agent according to claim 2, wherein the anti-EGFR antibody is cetuximab, panitumumab, or necitumumab.

5. A method for treatment of an EGFR gene mutations-positive non-small cell lung cancer, comprising:
   detecting a mutation; and
   when the mutation is detected, administrating a therapeutic agent comprising brigatinib, AP26113-analog, or AZD3463 as an active ingredient,
   wherein the mutation to be detected is at position 797 of EGFR.

6. The method for treatment of the EGFR gene mutations-positive non-small cell lung cancer, according to claim 5, wherein the mutation to be detected is at positions 797 and 790 of EGFR.

7. A method for treatment of an EGFR gene mutations-positive non-small cell lung cancer, comprising detecting the mutation at position 797 of EGFR and administrating the therapeutic agent according to claim 1.

8. A method for treatment of the EGFR gene mutations-positive non-small cell lung cancer, comprising detecting the mutations at positions 790 and 797 of EGFR and administrating the therapeutic agent according to claim 2.

9. A method for treatment of the EGFR gene mutations-positive non-small cell lung cancer, comprising detecting the mutation at position 797 of EGFR and administrating the therapeutic agent according to claim 3.

10. A method for treatment of the EGFR gene mutations-positive non-small cell lung cancer, comprising detecting the mutations at positions 790 and 797 of EGFR and administrating the therapeutic agent according to claim 4.

* * * * *